(12) United States Patent
Yuta

(10) Patent No.: US 7,725,413 B2
(45) Date of Patent: May 25, 2010

(54) GENERATING TWO-CLASS CLASSIFICATION MODEL FOR PREDICTING CHEMICAL TOXICITY

(75) Inventor: Kohtarou Yuta, Kawasaki (JP)

(73) Assignee: Fujitsu Limited, Kawasaki (JP)

(*) Notice: Subject to any disclaimer, the term of this patent is extended or adjusted under 35 U.S.C. 154(b) by 0 days.

(21) Appl. No.: 12/453,247

(22) Filed: May 4, 2009

(65) Prior Publication Data
US 2009/0222390 A1    Sep. 3, 2009

Related U.S. Application Data

(63) Continuation of application No. PCT/JP2007/056412, filed on Mar. 27, 2007.

(30) Foreign Application Priority Data
Nov. 13, 2006    (JP) .............................. 2006-307277

(51) Int. Cl.
G06F 15/18    (2006.01)
G06E 1/00    (2006.01)
(52) U.S. Cl. .............................. 706/20; 706/47; 706/61
(58) Field of Classification Search ........................ None
See application file for complete search history.

(56) References Cited

U.S. PATENT DOCUMENTS

| | | | | |
|---|---|---|---|---|
| 5,926,804 A | * | 7/1999 | Tufts et al. | 706/25 |
| 6,714,925 B1 | * | 3/2004 | Barnhill et al. | 706/48 |
| 6,760,715 B1 | * | 7/2004 | Barnhill et al. | 706/16 |
| 6,789,069 B1 | * | 9/2004 | Barnhill et al. | 706/12 |
| 6,882,990 B1 | * | 4/2005 | Barnhill et al. | 706/16 |

FOREIGN PATENT DOCUMENTS

| | | |
|---|---|---|
| JP | 6-124349 | 5/1994 |
| JP | 2005-352997 | 12/2005 |

OTHER PUBLICATIONS

Kotaro Yuda, "K-step Yard sampling method no kaihatsu to ADME-T Yosoku eno Tekiyo", Kozo Kassei Sokan Symposium Koen Yoshishu Nov. 7, 2006, vol. 34, pp. 29 to 30.

(Continued)

Primary Examiner—David R Vincent
Assistant Examiner—Ola Olude-Afolabi
(74) Attorney, Agent, or Firm—Staas & Halsey LLP

(57) ABSTRACT

A method includes: a) preparing as training data a sample set that contains a plurality of samples belonging to a first class and a plurality of samples belonging to a second class; b) generating, by performing discriminant analysis on the sample set, a first discriminant function having a high classification characteristic for the first class and a second discriminant function having a high classification characteristic for the second class; c) by classifying the sample set using the first and second discriminant functions, isolating any sample whose classification results by the first and second discriminant functions do not match; d) forming a new sample set by grouping together any sample thus isolated, and repeating b) and c) by using the new sample set; and e) causing d) to stop when the number of samples each of whose classification results do not match in c) has decreased to or below a predetermined value.

20 Claims, 16 Drawing Sheets

OTHER PUBLICATIONS

Kotaru Yuda, "Green Chemistry to ADMEWORKS", Fujitsu, Nov. 10, 2003, vol. 54, No. 6, pp. 471 to 479.

Masato Kitajima, et al., "Integrated High-Speed and Virtual In-Silico Screening which carries out Simlutaneous Evaluation of Pharmacological Activity and ADMET (II): NTP Carcinogenicity Data," Proceedings of the 30th Structure Activity Relationship Symposium, p. 37, Toyohashi, 2002.

International Search Report for International Application PCT/JP2007/056412, mailed May 22, 2007.

* cited by examiner

Fig.7

| 73 | 70 A Structure | 71 B CAS Number | 72 C Ames test |
|---|---|---|---|
| 1 | | 994-05-8 | nonmutagen (−) |
| 2 | | 99-82-1 | nonmutagen (−) |
| 3 | | 99-76-3 | nonmutagen (−) |
| 4 | | 98-00-0 | mutagen (+) |
| 5 | | 7939.mol | mutagen (+) |

Fig.8
| | A Structure | B Molecular Mass (Whole Molecule) | C Molecular Surface Area (Whole Molecule) | D Molecular Volume (Whole Molecule) | E Kappa 1 index (Whole Molecule) | F log P (Whole Molecule) | G Shape Flexibility index (Whole Molecule) | H Randic Topological index (Whole Molecule) |
|---|---|---|---|---|---|---|---|---|
| 1 |  | 102.2 (x11) | 143.704 (x21) | 91.8144 (x31) | 7 | 1.3154 | 2.30088 | 3.12132 |
| 2 |  | 140.3 (x12) | 190.412 (x22) | 129.174 (x32) | 8.1 | 3.7656 | 2.76071 | 4.69838 |
| 3 |  | 152.16 (x13) | 172.868 | 101.168 | 9.09091 | 1.4923 | 2.35543 | 5.23638 |
| 4 |  | 98.11 (x14) | 120.712 | 68.9598 | 5.14286 | 0.4597 | 1.24264 | 3.43185 |
| 5 |  | 123.17 (x15) | 152.166 | 89.6854 | 7.11111 | | 1.48936 | 4.18154 |

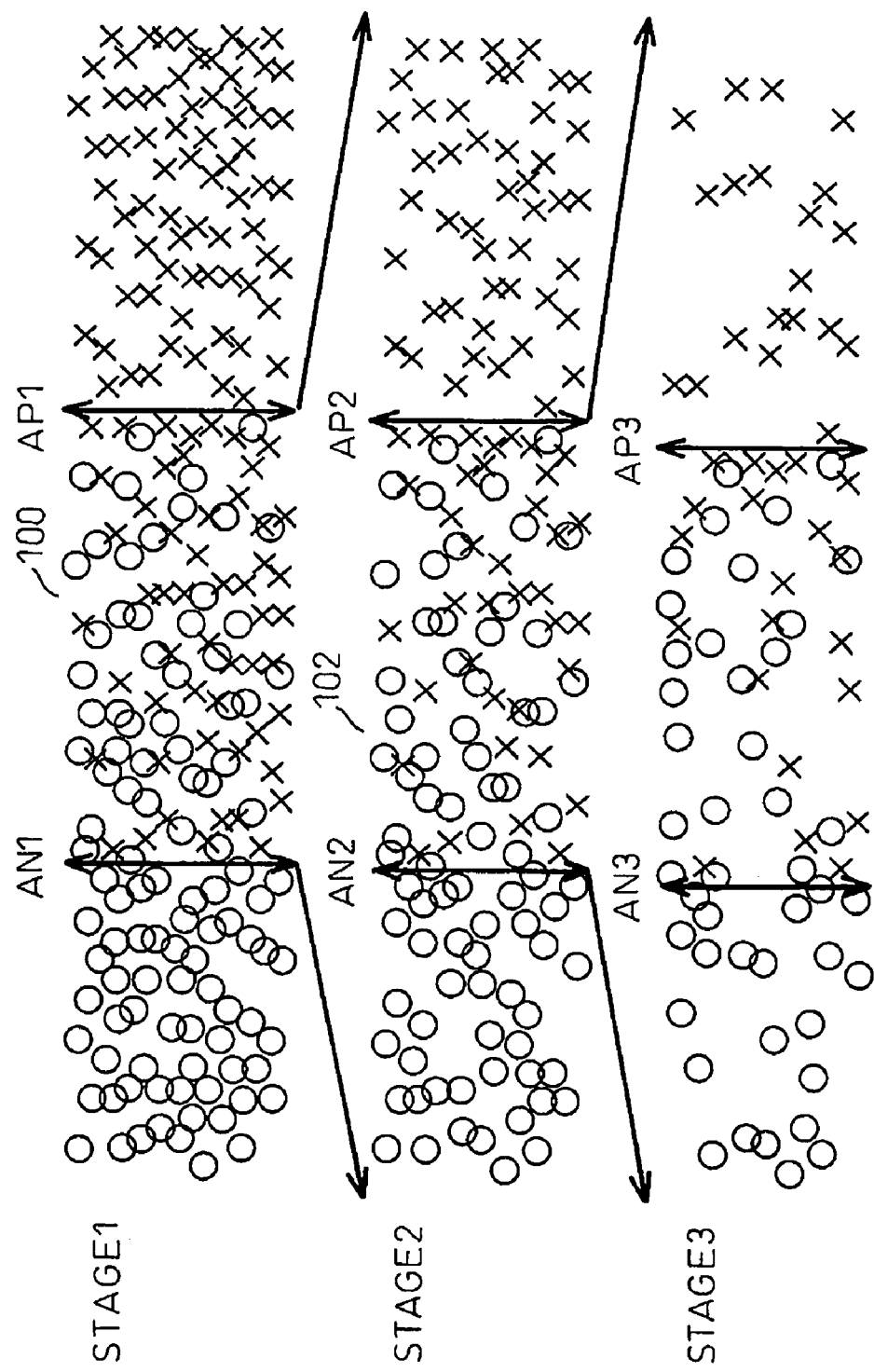

Fig.11

| SAMPLE NUMBER | CLASS INFORMATION FOR STAGE 1 | | | CLASS INFORMATION FOR STAGE 2 | | | CLASS INFORMATION FOR STAGE 3 | | | CLASS INFORMATION FOR STAGE 4 | | | CLASS INFORMATION FOR STAGE 5 | | | FINALLY DETERMINED CLASS |
|---|---|---|---|---|---|---|---|---|---|---|---|---|---|---|---|---|
| | AP 1 | AN 1 | 110 | AP 2 | AN 2 | 111 | AP 3 | AN 3 | 112 | AP 4 | AN 4 | 113 | AP 5 | AN 5 | 114 | 115 |
| 1 | − | − | GRAY | − | + | GRAY | − | + | GRAY | − | − | GRAY | | | | CLASS 2 |
| 2 | − | − | CLASS 2 | − | − | | | | | | | CLASS 2 | | | | CLASS 2 |
| 3 | − | + | GRAY | + | − | GRAY | + | − | GRAY | − | − | GRAY | | | | CLASS 2 |
| 4 | + | − | GRAY | + | − | GRAY | + | + | CLASS 1 | | | | + | + | CLASS 1 | CLASS 1 |
| 5 | + | − | GRAY | − | − | GRAY | + | + | | − | + | CLASS 2 | | | | CLASS 1 |
| ... | | | | | | | | | | | | | | | | |
| n−1 | − | − | GRAY | − | + | GRAY | − | − | GRAY | + | − | GRAY | | | | CLASS 2 |
| n | + | − | GRAY | − | + | GRAY | + | − | GRAY | − | − | GRAY | + | + | CLASS 1 | CLASS 1 |

Fig.12

| STAGE1 | STAGE2 | STAGE3 | ... | STAGEn |
|--------|--------|--------|-----|--------|
| AP1    | AP2    | AP3    | ... | APn    |
| AN2    | AN2    | AN3    | ... | ANn    |

O : Positive  
× : Negative

O : Positive  
× : Negative

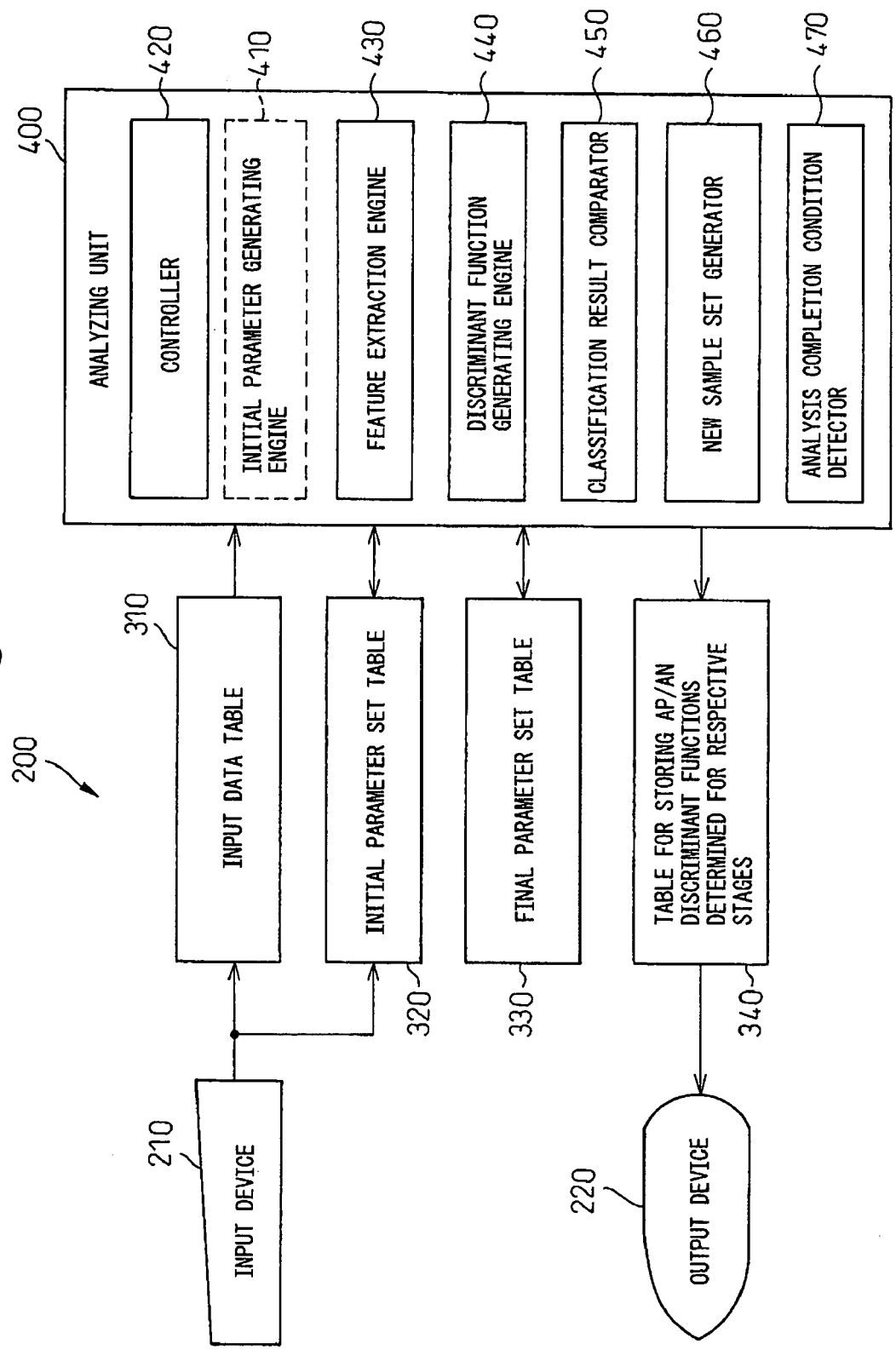

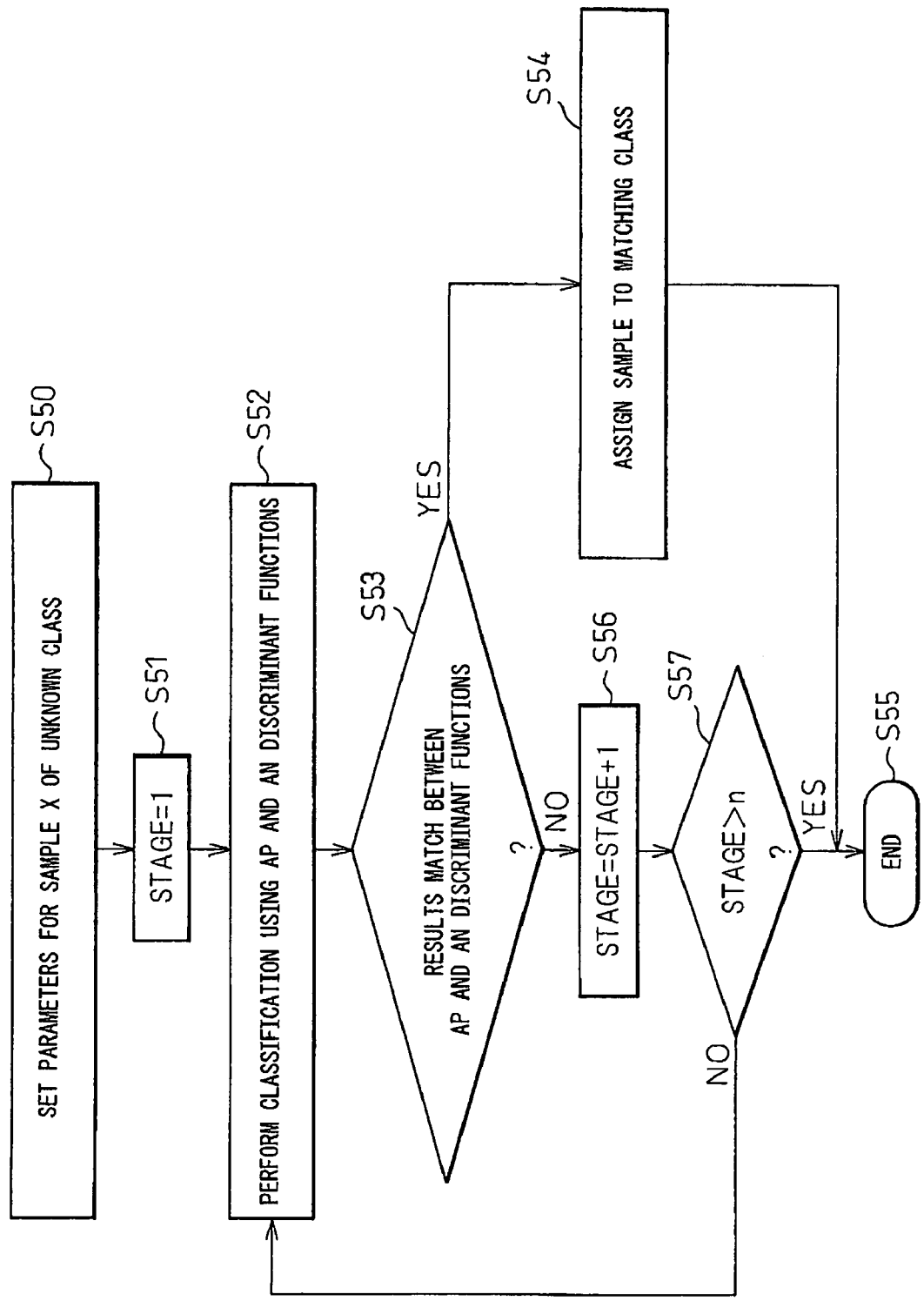

GENERATING TWO-CLASS CLASSIFICATION MODEL FOR PREDICTING CHEMICAL TOXICITY

CROSS-REFERENCE TO RELATED APPLICATIONS

The present application is a continuation application based on International application No. PCT/JP2007/056412, filed on Mar. 27, 2007.

TECHNICAL FIELD

The present invention relates to a method, program, and apparatus for generating a classification/prediction model for samples of unknown classes.

BACKGROUND OF THE INVENTION

Field of the Invention

A classification problem is a problem that, from a set of samples for which the classes they belong to are known, a rule is learned for classifying the samples into the classes and, using the thus learned rule as a prediction model, predicts the classes to which samples whose classes are not known belong. Among others, a two-class classification which classifies a sample set into two classes has long been used in structure-activity relationship research and, in recent years, has been attracting attention as a useful technique for testing chemicals for toxicity, etc. Methods for learning rules, that is, classification methods, include linear discriminant analysis methods such as linear learning machine, discriminant analysis, Bayes linear discriminant analysis, SVM (Support Vector Machine), AdaBoost, etc., and nonlinear discriminant analysis methods such as Bayes nonlinear discriminant analysis, neural networks, KNN (K-Nearest Neighbor), etc.

Generally, in a classification problem, misclassification always occurs, and it is extremely difficult to achieve a classification rate of 100%. Here, the "classification rate" is a measure that indicates how correctly samples for which the classes they belong to are known have been classified, while the "prediction rate" is a measure that indicates how correctly samples for which the classes they belong to are not known have been classified. Basically, the "classification rate" is not lower than the "prediction rate." Accordingly, the upper limit of the "prediction rate" automatically increases as the "classification rate" is raised. This means that if the classification rate can be raised, the prediction rate improves. Further, from the general characteristics of data analysis, it is known that the classification rate drops as the number of samples increases. A misclassification is an instance in which a sample that belongs to class 1, for example, is wrongly classified as a sample belonging to class 2. For example, when classifying a sample set including a plurality of chemicals into two classes containing a toxic chemical set (class 1) and a nontoxic chemical set (class 2), since the factors contributing to the manifestation of toxicity are complex and diverse, misclassification can easily occur and, with the current state of the art, it is extremely difficult to raise the classification rate.

It is also noted that no matter how high the classification rate is made, if the number of samples used is large, the absolute number of misclassified samples becomes large. For example, when classifying toxic chemicals and nontoxic chemicals, if the number of samples used for training is large, for example, if the classification is to be performed using 10000 chemicals, a classification rate of 90% would mean that 1000 chemicals were misclassified, the number being large enough to become a problem. Furthermore, when classifying toxic chemicals, if chemicals having no toxicity were misclassified as chemicals having toxicity, it would not present a serious problem, but it would be very dangerous if chemicals having toxicity were misclassified as chemicals having no toxicity, and such a misclassification must be avoided by all means. From this point also, it is desirable that the classification rate be increased to 100%.

It is now recognized that increasing the classification rate for a classification problem is of utmost concern, and various efforts have been expended for this purpose. Usually, classification is performed using one discriminant function for each one sample set, but there is proposed a classification rate enhancing method which enhances an apparent classification rate by performing classification using a plurality of discriminant functions constructed by different classification techniques. The case where classification is performed using only one discriminant function and the case where classification is performed using a plurality of discriminant functions will be described below with reference to drawings. In the drawings given hereinafter, the same reference numerals indicate the same or similar component elements, and the description of such component elements, once given, will not be repeated thereafter.

FIG. 1 is a diagram depicting in the form of an image the results of two-class classification when a sample set is ideally classified into two classes by using only one discriminant function. Since a number, N, of parameters (explanatory variables) are used for the classification, the diagram depicts the case where the samples are classified in N-dimensional space into two classes, i.e., a positive class (class 1, for example, a toxic class) and a negative class (class 2, for example, a nontoxic class). In FIG. 1, each white dot indicates a sample that is normally classified into the positive class, and each X indicates a sample that is normally classified into the negative class. In the ideal classification, that is, when the classification rate is 100%, the discriminant function (prediction model) 1 perfectly separates the originally positive samples 2 and the originally negative samples 3. However, such an ideal classification cannot be readily realized in a two-class classification that classifies toxic chemicals and nontoxic chemicals.

FIG. 2 depicts the results of a conventional two-class classification performed using only one discriminant function. In this case, a number of samples 3' that is normally classified as negative samples located to the right of the discriminant function 1 are located to the left of the discriminant function 1, i.e., in the region that normally contains only positive samples. Similarly, a number of samples 2' that are normally classified as positive samples located to the left of the discriminant function 1 are located to the right of the discriminant function 1, i.e., in the region that normally contains only negative samples. Samples 2' and 3' are misclassified samples, the presence of which contributes to reducing the classification rate. With the present state of the art of discriminant analysis, it is difficult to reduce the number of such misclassified samples 2' and 3' to zero (to achieve a classification rate of 100%). In particular, when factors causing toxicity are complex, and the number of samples are large, as in the case of screening for toxic chemicals, it is virtually impossible to achieve a classification rate of 100%.

FIG. 3 depicts an example of classification that uses a plurality of discriminant functions 1a, 1b, and 1c derived by different classification techniques. In the illustrated example, three discriminant functions are used, but two discriminant functions 1a and 1b or 1c may be used. When using a plurality of discriminant functions, it is necessary to set a rule for determining the classes. In the case of classification that uses two discriminant functions, when the classification results of a sample by the two discriminant functions match, the sample is classified as belonging to the class indicated by the results, that is, one of the originally intended two classes. On the other hand, the classification results produced by the two discriminant functions are different, the sample is classified. In this case, the sample is mapped to a class that is different from the originally intended two classes (for convenience, such a class will be referred to as gray class). On the other hand, when using three or more discriminant functions, if the number of them is odd, a majority rule can be applied, so that the classes can be determined by setting a finer class-determining rule.

In the case of classification using a plurality of discriminant functions, the samples are classified between a sample set (A) in which each sample is assigned the same class by the different discriminant functions and a sample set (B) in which each sample is assigned different classes by the different discriminant functions. Since the classification rate represents only the classification results of the samples in the sample set (A) by excluding the sample set (B) from the whole sample set, the apparent classification rate improves. However, since the classification is not done on the sample set (B), the classification is far from perfect when viewed from the whole sample set (A+B), and it merely achieves an improvement in apparent "classification rate." Generally, in the case of classification using a plurality of discriminant functions, as the size of the sample set difficult to classify increases, the percentage of the samples whose classes are not determined (that is, gray class samples) increases. There can occur cases where the percentage of the gray class samples exceeds 90%. In such cases, the classification rate, however high it may be, is of no use in practice because the class determination rate is extremely low.

However, even when a plurality of discriminant functions derived by different classification techniques are used, it is still difficult to classify the sample set in a perfectly correct manner. The reason is that, as depicted in FIG. 3, in whatever way the three discriminant functions $1a$, $1b$, and $1c$ are combined, there still occur negative samples (indicated by Xs) located to the left of the discriminant functions $1a$, $1b$, and $1c$ and positive samples (indicated by white dots) located to the right of the discriminant functions $1a$, $1b$, and $1c$. In other words, even when a plurality of different discriminant functions are used, it is difficult to achieve an extremely high classification rate.

As earlier described, if chemicals actually having no toxicity were misclassified as chemicals having toxicity, it would not present a serious problem, but misclassifying a toxic chemical as a nontoxic chemical (referred to as a false negative) is unacceptable. In view of this, the present inventor constructed a discriminant function that was deliberately made highly sensitive to chemicals having toxicity (carcinogenicity) (refer to non-patent document 1). With this discriminant function, the overall classification rate was not very high, but the probability of false negatives occurring was successfully reduced. However, even with this method, it was not possible to reduce the probability of the occurrence of false negatives to zero.

Non-patent document 1: Masato Kitajima, Jose Martin Ciloy, and Kohtaro Yuta, "Integrated High-Speed and Virtual In-Silico Screening which Carries Out Simultaneous Evaluation of Pharmacological Activity and ADMET (II): NTP Carcinogenicity Data," Proceedings of the 30th Structure-Activity Relationship Symposium, p. 37, Toyohashi, 2002.

PROBLEMS TO BE SOLVED BY THE INVENTION

The present invention has been devised to overcome the above-described problems associated with the prior known two-class classification problems, and an object of the invention is to provide a method, program, and apparatus for generating discriminant functions, i.e., a classification/prediction model, that can achieve a classification rate as close as possible to 100%, irrespective of differences in classification technique. It is another object of the invention to provide a method for generating a chemical toxicity prediction model having high reliability.

MEANS FOR SOLVING THE PROBLEMS

According to a first aspect, to solve the above problems, there is provided a method for generating a two-class classification/prediction model, including: a) preparing as training data a sample set that contains a plurality of samples belonging to a first class and a plurality of samples belonging to a second class; b) generating, by performing discriminant analysis on the sample set, a first discriminant function having a high classification characteristic for the first class and a second discriminant function having a high classification characteristic for the second class; c) by classifying the sample set using the first and second discriminant functions, isolating any sample whose classification results by the first and second discriminant functions do not match; repeating b) and c) by using a new sample set which is formed by grouping together any sample isolated in c); and e) causing the d) to stop when the number of samples, each of whose classification results do not match in c), has decreased to or below a predetermined value or when the number of repetitions or processing time for repetitions has reached or exceeded a predetermined value, and wherein the first and second discriminant functions determined in b) are set up as a classification/prediction model for samples of unknown classes.

In the first aspect, first the training data is constructed using samples known to belong to the first class and samples known to belong to the second class. Then, by performing discriminant analysis on the training data, the first discriminant function that achieves a high classification rate, for example, a classification rate of substantially 100%, for the first class and the second discriminant function that achieves a high classification rate, for example, a classification rate of substantially 100%, for the second class are generated. Next, the objective variable of each sample is calculated using the two discriminant functions, and samples each of whose values of the objective variable, i.e., classification results, match between the two discriminant functions and samples each of whose results do not match are identified.

Since the two discriminant functions provide a classification rate of nearly 100% for the first and second classes, respectively, any sample whose classification results match between the two discriminant functions is identified as a correctly classified sample. Accordingly, any sample whose classification results match is assigned to class 1 or class 2, whichever is identified. On the other hand, any sample whose classification results do not match is assigned to the gray class.

In this aspect, when the gray class for the first stage is thus formed, the samples assigned to the gray class are grouped together to form a new sample set. Then, the two discriminant functions are generated for this sample set, to classify the samples. As a result, the gray class for the second stage is formed. Thereafter, the gray class for the third stage, the gray class for the fourth stage, etc., are formed in a similar manner. The gray class formation is repeated until the number of samples assigned to the gray class finally decreases to zero.

When the number of samples assigned to the gray class has decreased to zero, all the samples have been correctly classified. That is, a classification rate of 100% is achieved. In this aspect, the set of the discriminant functions generated in each gray class forming stage is set up as a two-class classification/prediction model.

According to a second aspect, to solve the above problems, there is provided a program for generating a two-class classification/prediction model, the program causing a computer to perform a process including: a) preparing as training data a sample set that contains a plurality of samples belonging to a first class and a plurality of samples belonging to a second class; b) generating, by performing discriminant analysis on the sample set, a first discriminant function having a high classification characteristic for the first class and a second discriminant function having a high classification characteristic for the second class; c) by classifying the sample set using the first and second discriminant functions, isolating any sample whose classification results by the first and second discriminant functions do not match; d) repeating b) and c) by using a new sample set which is formed by grouping together any sample isolated in c); and e) causing d) to stop when the number of samples each of whose classification results do not match in c) has decreased to or below a predetermined value or when the number of repetitions or processing time for repetitions has reached or exceeded a predetermined value.

According to a third aspect, to solve the above problems, there is provided a method for generating a chemical toxicity prediction model, including: a) preparing as training data a sample set that contains a plurality of chemicals belonging to a first class and a plurality of chemicals belonging to a second class, wherein the chemicals in the first class have a specific kind of toxicity and the chemicals in the second class do not have the toxicity; b) generating, by performing discriminant analysis on the sample set, a first discriminant function having a high classification characteristic for the first class and a second discriminant function having a high classification characteristic for the second class; c) by classifying the sample set using the first and second discriminant functions, isolating any chemical whose classification results by the first and second discriminant functions do not match; d) repeating b) and c) by using a new sample set which is formed by grouping together any chemical isolated in c); and e) causing d) to stop when the number of chemicals each of whose classification results do not match in c) has decreased to or below a predetermined value or when the number of repetitions or processing time for repetitions has reached or exceeded a predetermined value, and wherein the first and second discriminant functions determined in b) after completion of d) are set up as a classification/prediction model for chemicals of unknown classes.

In the first, second, and third aspects described above, the first discriminant function may be generated by carrying out: f) generating an initial discriminant function by performing discriminant analysis on the sample set; g) forming a new sample set by removing from the sample set any sample misclassified by the initial discriminant function as being a sample belonging to the first class when the sample is actually a sample belonging to the second class, and generating a new discriminant function by performing discriminant analysis on the new sample set; and h) repeating g) by using the new discriminant function from g) as the initial discriminant function, until the number of samples misclassified into the first class by the initial discriminant function decreases to substantially zero, while on the other hand, the second discriminant function may be generated by carrying out: i) generating an initial discriminant function by performing discriminant analysis on the sample set; j) forming a new sample set by removing from the sample set any sample misclassified by the initial discriminant function as being a sample belonging to the second class when the sample is actually a sample belonging to the first class, and generating a new discriminant function by performing discriminant analysis on the new sample set; and k) repeating j) by using the new discriminant function from j) as the initial discriminant function, until the number of samples misclassified into the second class by the initial discriminant function decreases to substantially zero.

Further, the initial discriminant function and the new discriminant function may each be generated by performing feature extraction on an initial parameter set pregenerated for the sample set prepared as the training data, thereby forming a final parameter set, and by performing the discriminant analysis using the final parameter set.

The discriminant analysis method for generating the first discriminant function and the discriminant analysis method for generating the second discriminant function need not necessarily be the same, and the discriminant method for determining the gray class in each stage may differ from one stage to another.

According to a fourth aspect, to solve the above problems, there is provided an apparatus for generating a two-class classification/prediction model, including: an input device entering as training data a sample set that contains a plurality of samples belonging to a first class and a plurality of samples belonging to a second class; a discriminant function generating device generating, by performing discriminant analysis on the sample set, a first discriminant function having a high classification characteristic for the first class and a second discriminant function having a high classification characteristic for the second class; a classification result comparing device classifying the sample set by using the first and second discriminant functions, and isolating any sample whose classification results by the first and second discriminant functions do not match; and a control device forming a new sample set by grouping together any sample isolated by the classification result comparing device, and causing the discriminant function generating device and the classification result comparing device to operate repeatedly, and wherein the control device causes the repeating operation to stop when the number of samples each of whose classification results do not match in the classification result comparing device has decreased to or below a predetermined value or when the number of repetitions or processing time for repetitions has reached or exceeded a predetermined value.

EFFECT OF THE INVENTION

As described above, the present method can achieve a classification rate substantially equal to 100% for two-class classification, regardless of the kind of classification technique used. Even when the number of samples is large, and the number of samples assigned to the gray class by the initial discriminant analysis is therefore large, by increasing the number of gray class forming stages all the samples can eventually be assigned to the correct classes. That is, with the classification method of the present invention, the classification rate does not decrease with increasing number of samples. Even when classifying an enormous number of samples, perfect classification could be accomplished. Since the "classification rate" of 100% can be raised to its upper limit of 100%, the upper limit of the "prediction rate" also increases.

Further, according to the chemical toxicity prediction method, even when the number of training samples used for toxicity prediction is as large as several thousands to tens of thousands, for example, the classification rate substantially equal to 100% can be achieved for these samples; accordingly, by increasing the size of the sample population, the present invention can provide a highly reliable chemical toxicity prediction model that can detect with extremely high reliability the presence or absence of toxicity in chemicals for which the presence or absence of toxicity is unknown.

As mentioned before, in toxicity prediction, misclassifying a toxic chemical as a nontoxic chemical would lead to a very dangerous situation. The method of the present invention can reduce the probability of such misclassification to an infinitesimally small value. As a result, the method can provide a tool having a high classification/prediction rate capable of conforming to the REACH regulation expected to be enforced by the EU Parliament. In the REACH regulation, proposals are under study that oblige every use to evaluate the toxicity of chemicals by the IT, and the need to develop a method that achieve a high classification rate and a high prediction rate is pressing and of utmost concern. In view of these problems, by using the method of the present invention a chemical toxicity prediction model can be provided that has extremely high reliability demanded by the REACH regulation.

BRIEF DESCRIPTION OF THE DRAWINGS

FIG. 7 is a diagram depicting one example of a data table for storing sample data.

FIG. 8 is a diagram depicting one example of a table for storing final parameter set data.

FIG. 10 is an image diagram depicting a procedure for performing classification by forming a new sample set using gray samples.

FIG. 11 a data table for storing the process of assigning samples to respective classes.

FIG. 12 is a table for storing classification/prediction models.

FIG. 19 is a diagram depicting the system configuration of a classification/prediction model generating apparatus according to one embodiment of the present invention.

FIG. 20 is a flowchart illustrating a procedure for performing the classification/prediction of samples of unknown classes by using the classification/prediction model generated by the method according to the one embodiment of the present invention.

DESCRIPTION OF THE REFERENCE NUMERALS

Figure 1:
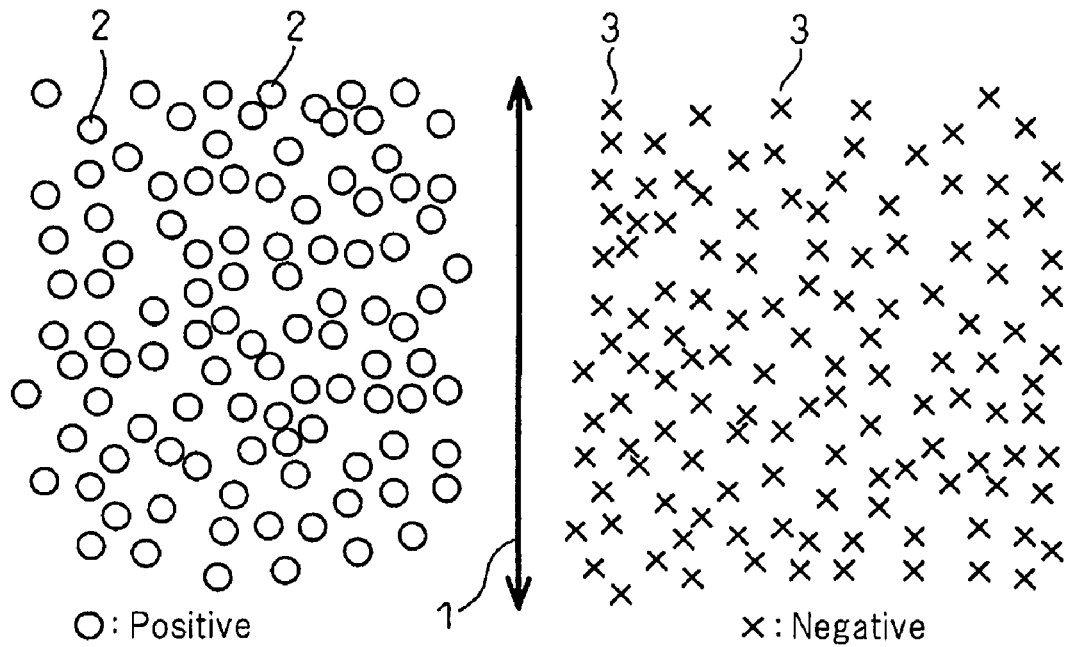
FIG. 1 is an image diagram depicting the results of an ideal two-class classification.

10 . . . AP discriminant function
20 . . . AN discriminant function
90 . . . initial discriminant function
92 . . . misclassified negative sample
94 . . . misclassified positive sample
100, 102 . . . gray class
200 . . . two-class classification/prediction model generating apparatus
210 . . . input device
220 . . . output device
310 . . . input data table
320 . . . initial parameter set table
330 . . . final parameter set table
340 . . . table for storing AP/AN discriminant functions determined for respective stages
400 . . . analyzing unit
410 . . . initial parameter generating engine
420 . . . controller
430 . . . feature extraction engine
440 . . . discriminant function generating engine
450 . . . classification result comparator
460 . . . new sample set generator
470 . . . analysis completion condition detector

BEST MODE FOR CARRYING OUT THE INVENTION

Classification Principle of the Invention

Before describing the embodiments of the present invention, the classification principle of the present invention will be described first.

Figure 2:
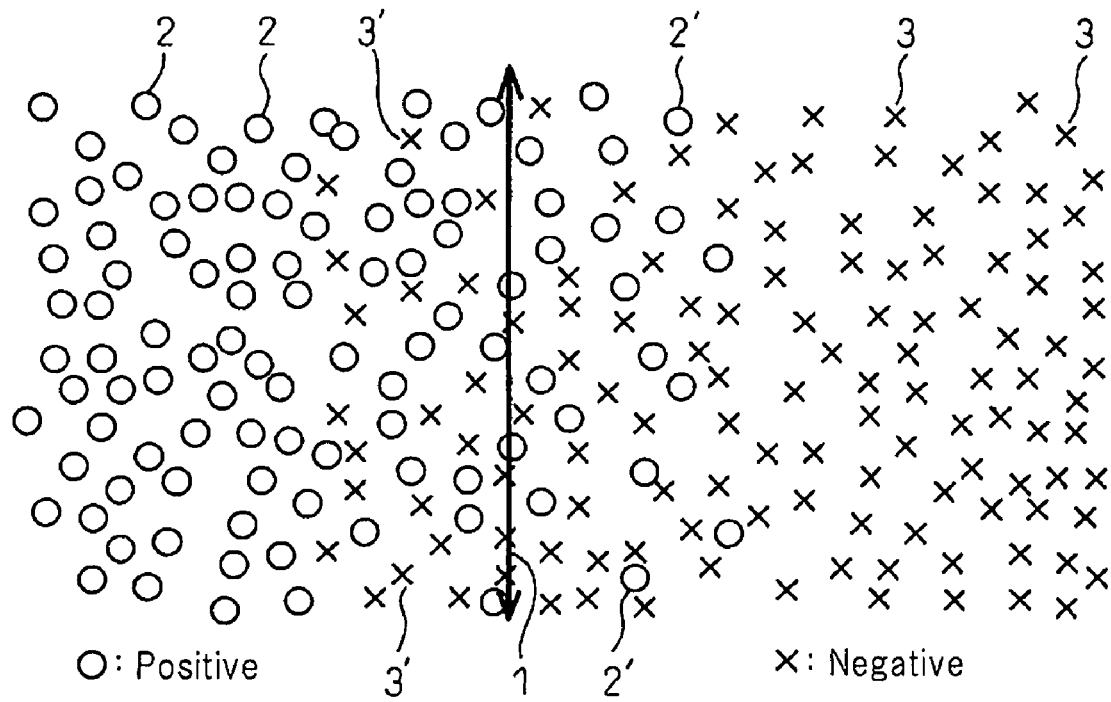
FIG. 2 is an image diagram depicting the results of a conventional two-class classification.
Figure 3:
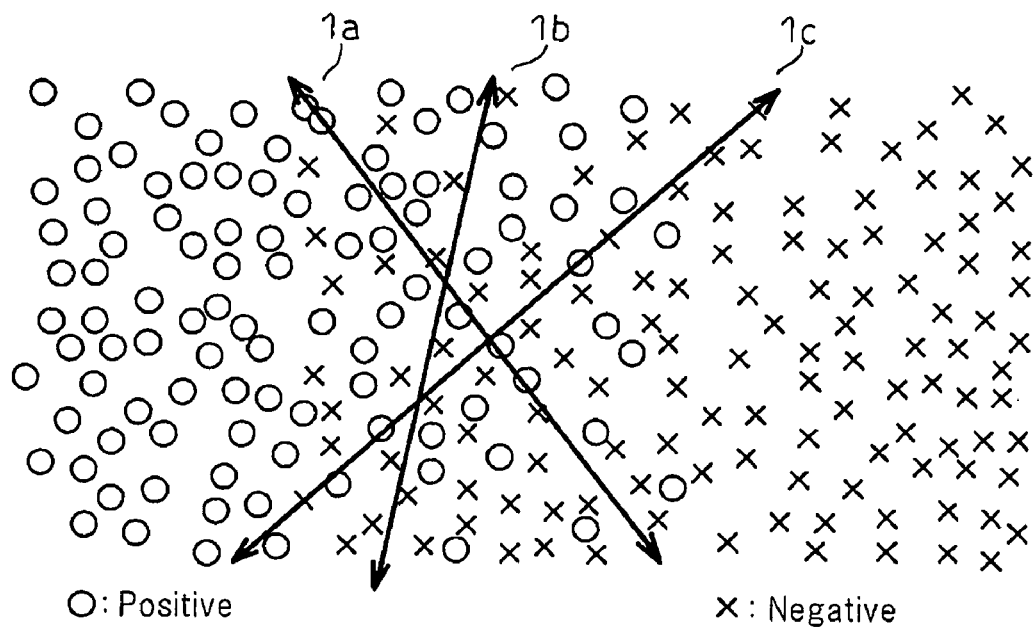
FIG. 3 is an image diagram depicting the results of a prior art two-class classification using three different kinds of discriminant functions.
Figure 4:
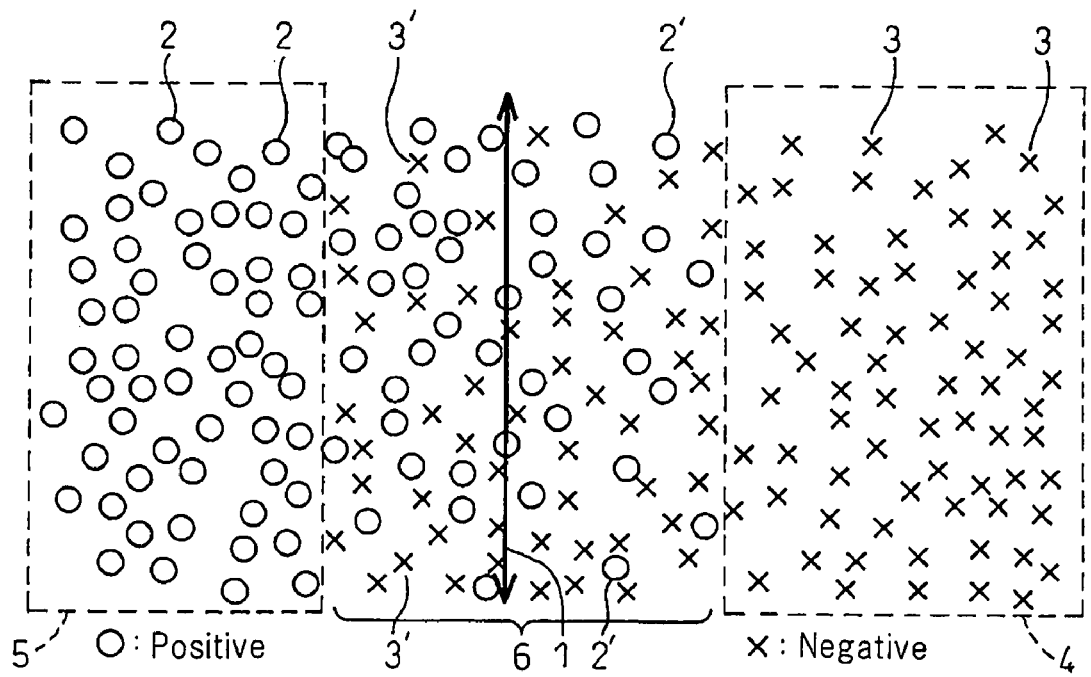
FIG. 4 is an image diagram serving to illustrate the basic principle of the present invention.

FIG. 4 is a diagram depicting the results of a conventional two-class classification, which is the same as that depicted in FIG. 2. In the following description, class 1 is designated as positive class and class 2 as negative class for simplicity of description, but it will be appreciated that the present invention is applicable to any kind of two-class classification. In the case of the discriminant function 1 obtained as a result of the two-class classification, misclassified samples 2' and 3' occur from both positive and negative samples. In the N-dimensional sample space depicted here, when attention is paid to the regions 4 and 5 enclosed by dashed lines, the region 4 does not contain any misclassified positive samples but only contains correctly classified negative samples 3. Similarly, the region 5 does not contain any misclassified negative samples but only contains correctly classified positive samples 2. The intermediate region 6 between the regions 4 and 5 is a region that contains correctly classified samples and misclassified samples in a mixed manner.

In view of the presence of these regions, the present inventor camp up with the following idea. That is, if these regions 4, 5, and 6 could be accurately separated, then a second classification could be performed by excluding the correctly classified samples belonging to the regions 4 and 5 from the sample population and by setting new N-dimensional parameters for the samples belonging to the region 6. As a result of the second classification, a region that only contains correctly classified negative samples, a region that only contains correctly classified positive samples, and a region that contains misclassified samples would be obtained, as in the case of the first two-class classification. Then, by isolating a sample set in the region containing the misclassified samples, and by setting new N-dimensional parameters, a third two-class classification could be performed.

By repeating the two-class classification until the number of misclassified samples decreased to zero, all the initial samples would eventually be classified into the correct classes. The problem here would be how the regions 4, 5, and 6 depicted in FIG. 4 could be isolated. To address this, the present inventor considered using two discriminant functions. These discriminant functions are both designed for two-class classification, but the characteristics are totally different between the two functions.

Figure 5:
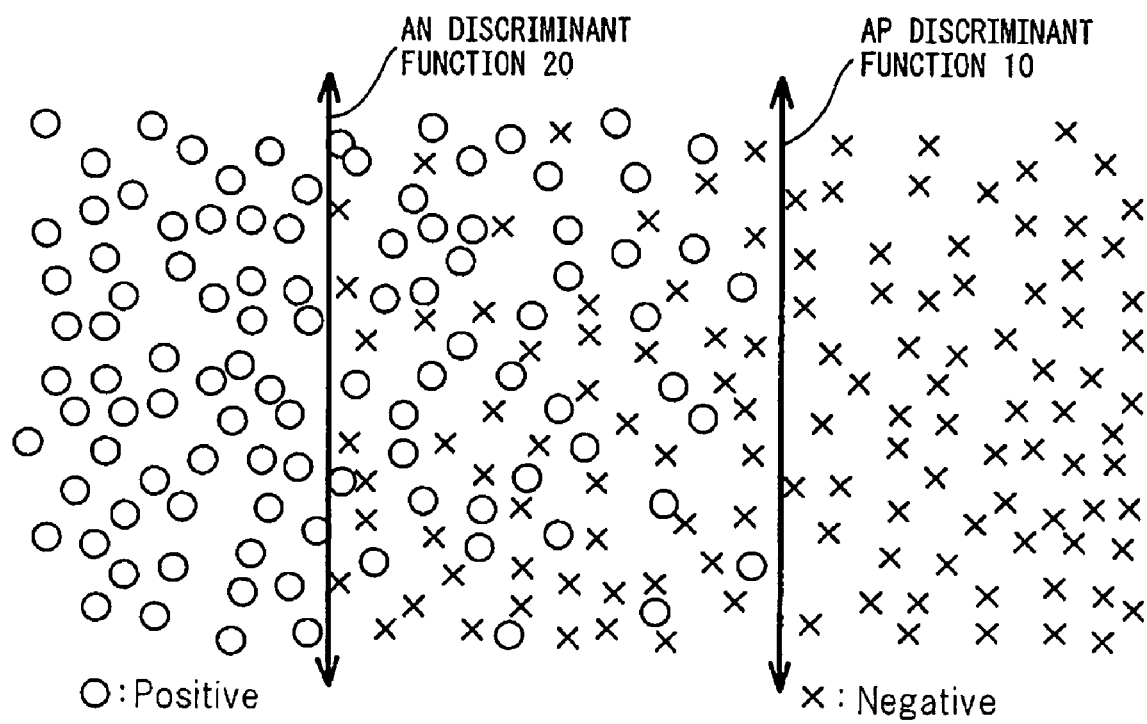
FIG. 5 is an image diagram for illustrating an AP discriminant function and an AN discriminant function according to the present invention.

FIG. 5 is a diagram illustrating the characteristics of the two discriminant functions used in the present invention. In the figure, the discriminant function 10 has the characteristic of being able to classify all the positive samples correctly because all the positive samples are located only on one side of the discriminant function. On the other hand, the discriminant function 20 can classify all the negative samples correctly because all the negative samples are located only on one side of the discriminant function. The discriminant function 10 will be called the all-positive (AP) discriminant function, and the discriminant function 20 the all-negative (AN) discriminant function. The AP discriminant function 10 classifies all the positive samples correctly, but a number of negative samples are misclassified because the negative samples are dispersed on both sides of the discriminant function. However, because all the positive samples are correctly classified, the samples classified as negative by the AP discriminant function 10 do not contain any misclassified positive samples. That is, the samples contained in the region to the right of the AP discriminant function 10 in FIG. 5 are all correctly classified negative samples. Accordingly, the samples classified as negative by the AP discriminant function 10 can be made to belong to the negative class, i.e., class 2, since the probability of misclassifying them is zero.

Similarly, the AN discriminant function 20 classifies all the negative samples correctly as negative, but a number of positive samples are misclassified. However, because all the negative samples are correctly classified, the samples classified as positive by the AN discriminant function 20 do not contain any misclassified negative samples. That is, the samples contained in the region to the left of the AN discriminant function 20 in FIG. 5 are all correctly classified positive samples. Accordingly, the samples classified as positive by the AN discriminant function 20 can be made to belong to the positive class, i.e., class 1, since the probability of misclassifying them is zero.

On the other hand, in FIG. 5, the intermediate region flanked by the AP discriminant function 10 and AN discriminant function 20 contains positive samples and negative samples in a mixed manner, and it is not possible to determine which of the classes the samples in this region is made to belong to. Accordingly, these samples are classified into the gray class, i.e., class 3. The second and third two-class classifications described earlier are performed on the samples belonging to the gray class, i.e., class 3. By repeating such two-class classification until the number of samples belonging to class 3 decreases to zero, theoretically all the samples contained in the initial population can be classified into the two classes with a classification rate of 100%.

FIG. 5 has depicted an image when the sample space is divided into three classes by using the AP discriminant function 10 and AN discriminant function 20, but the actual task of classifying the samples into the three classes is accomplished by performing two two-class classifications using the AP discriminant function 10 and AN discriminant function 20, thereby classifying any sample whose classification results match into a corresponding one of the originally intended two classes, while classifying any sample whose classification results do not match into class 3. This class 3 is a class newly set in accordance with the classification results as the class (gray class) to which the samples that are not classified by the two discriminant functions as belonging to either one of the originally intended two classes, class 1 and class 2, are made to belong. Accordingly, the classification according to the present invention is essentially two-class classification, and differs from three-class classification that, in the first place, classifies the samples into three different classes.

[Classification/Prediction Model Generation Method According to One Embodiment of the Present Invention]

One embodiment of the present invention will be described below while also dealing with the procedures for obtaining the AP discriminant function and AN discriminant function. The present invention is applicable regardless of the kind of classification technique. Accordingly, the same principle applies irrespective of differences in classification technique, whether it be linear discriminant analysis, nonlinear discriminant analysis, etc. For example, techniques such as linear learning machine, discriminant analysis, Bayes linear discriminant analysis, SVM (Support Vector Machine), AdaBoost, etc. can be used for linear discriminant analysis, and techniques such as Bayes nonlinear discriminant analysis, neural networks, etc. can be used for nonlinear discriminant analysis.

Figure 6:
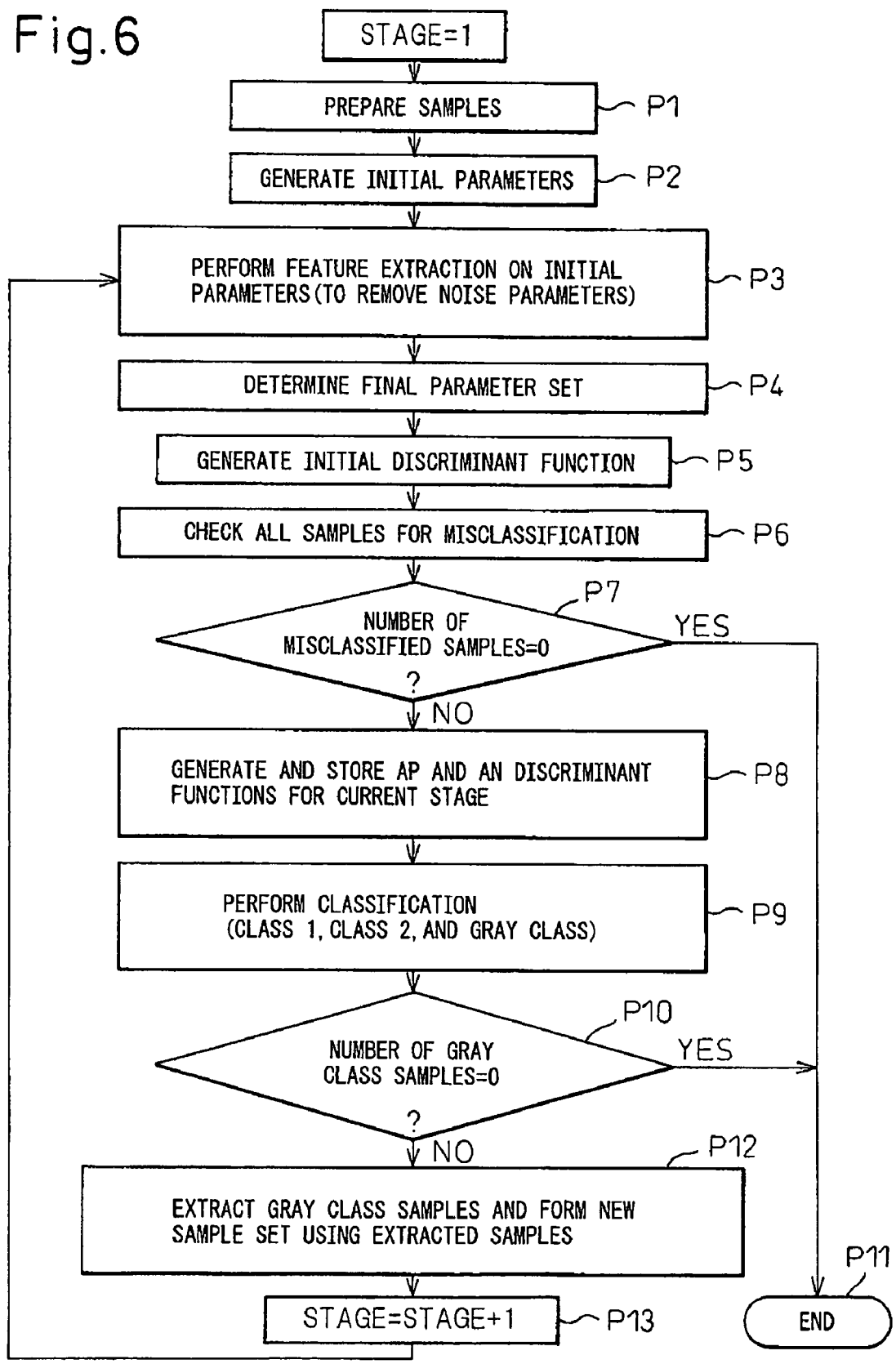
FIG. 6 is a flowchart illustrating a procedure of a classification/prediction model generation method according to one embodiment of the present invention.

FIG. 6 is a flowchart illustrating the entire procedure of the classification/prediction model generation method according to the one embodiment of the present invention. The procedure starts with STAGE 1, a first stage for isolating the gray class. In step P1, a plurality of samples whose values for the target characteristic are known are prepared. For example, 500 samples known to have a certain kind of toxicity, i.e., positive samples, and 500 samples known to not have that toxicity, i.e., negative samples, are prepared. The thus prepared samples are entered into a classification/prediction model generating apparatus, and a table for storing sample data, such as depicted in FIG. 7, is constructed.

In FIG. 7, column 70 depicts the two- or three-dimensional structural formula of each chemical as a sample. Column 71 depicts the CAS number of each chemical, and column 72 depicts the result of the Ames test. In column 72, "mutagen" indicates that the Ames test result depicts the sample has mutagenicity (+), while "nonmutagen" indicates that the sample does not have mutagenicity (−). The illustrated example depicts the data table used to classify the samples into two classes by classifying mutagenic samples as belonging to class 1 (positive class) and nonmutagenic samples as belonging to class 2 (negative class). Column 73 depicts sample number.

Next, in step P2, initial parameters, i.e., explanatory variables (x1, x2, ..., xx) for calculating objective variables, are generated. The initial parameters are automatically generated from the structure of each chemical. For example, ADME-WORKS ModelBuilder marketed by Fujitsu can generate 800 or more parameters based on the two- or three-dimensional structural formula and various properties of chemicals. In step P3, feature extraction is performed on the thus generated initial parameters to remove noise parameters unwanted for classification purposes. The final parameter set (x1, x2, ..., xn) is thus determined (step P4). The feature extraction can be performed using known techniques such as simple correlation coefficient, multiple correlation coefficient, frequency of occurrence, Fischer ratio, analysis of variance, etc. Various engines for feature extraction are also commercially available.

FIG. 8 is a table depicting the final parameter set selected as having effects on the Ames test results and numerical data of each individual chemical for the respective parameters. Column 80 depicts the structural formula of each chemical, and column 81 and subsequent columns depict the various parameters. For example, column 81 depicts the molecular mass of each chemical, column 82 depicts the molecular surface area, and column 83 depicts the value of log P, as the respective parameters. In the data table, the value carried in cell 84 is data indicating the molecular mass of sample 1, the value in cell 85 is data indicating the molecular surface area of sample 1, and the value in cell 86 is data indicating the value of log P of sample 1. The values carried in the respective cells provide the parameter data for the corresponding sample. Column 84 indicates the sample number of each sample.

Next, an initial discriminant function is generated (step P5) by performing discriminant analysis using the final parameter set generated in step P3. In the discriminant analysis, the discriminant function is given by the following equation (1).

$$Yk = a1 \cdot x1k + a2 \cdot x2k + a3 \cdot x3k + \ldots + an \cdot xnk + Const \quad (1)$$

In equation (1), Yk is the value of the objective variable for the k-th sample, x1k, x2k, x3k, ..., xnk are parameter (explanatory variable) data for the k-th sample, and a1, a2, a3, ..., an are the coefficients of the respective parameters. Const represents a constant. Parameter data x11, x21, x31, etc. are obtained for the data carried in the respective cells in FIG. 8. Accordingly, when the coefficients a1, a2, etc. of the respective parameters are obtained by the discriminant analysis, the value Y of the objective variable for each sample is calculated by substituting the data carried in the respective cells of the table of FIG. 8 into equation (1). Classification of the sample is performed using the value Y. In the example depicted in FIGS. 7 and 8, the discriminant function is generated so that the value of Y becomes negative in the case of nonmutagen and positive in the case of mutagen. Various engines for performing discriminant analysis are also commercially available.

Next, in step P6, all the samples are classified using the thus generated initial discriminant function, and the classification results are checked to determine whether the samples are correctly classified or not (step P7). To check the results, first the value of the objective variable Y is calculated for each sample by using the initial discriminant function, to assign the sample to the corresponding class, and after that, the class to which the sample is assigned is compared with the value actually measured on that sample. For example, in the input table data of FIG. 7, the Ames test result depicts that sample 1 is negative, which is the actually measured value. If the value of the objective variable Y calculated using the above initial discriminant function is negative, it is determined that sample 1 is correctly classified. On the other hand, the actually measured value of sample 4 is positive; here, if the objective variable Y is negative, it is determined that sample 4 is misclassified.

Figure 9:
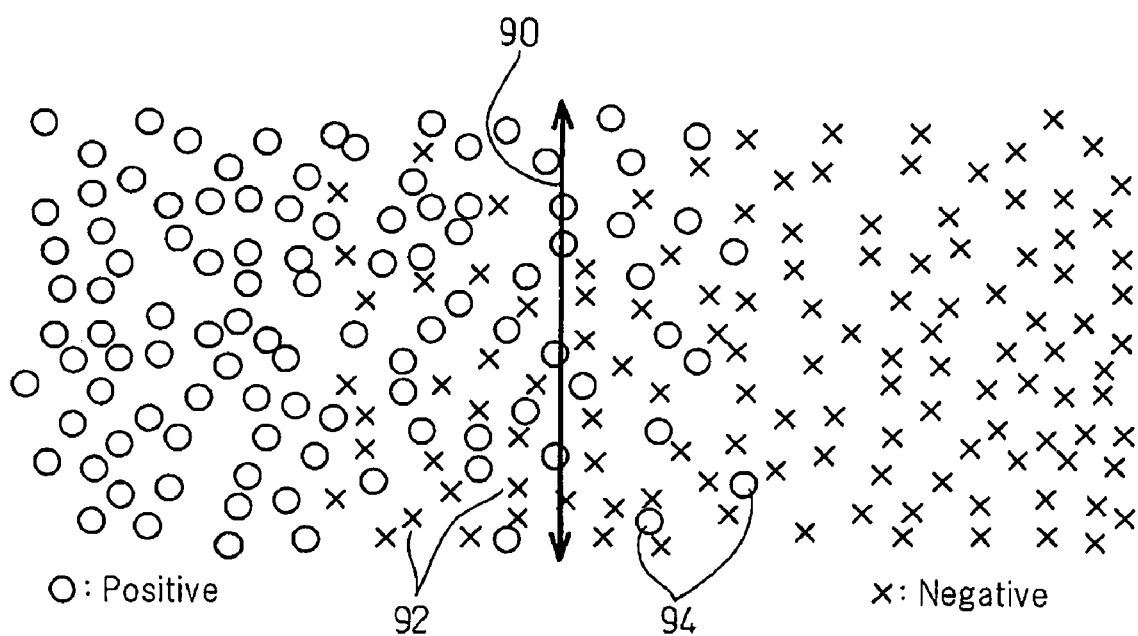
FIG. 9 is an image diagram depicting the relationship between an initial discriminant function and misclassified samples.

FIG. 9 is a diagram depicting in the form of an image the results of the classification performed using the initial discriminant function generated in step P5. In the figure, each white dot indicates a sample that is normally classified as positive, while each X indicates a sample that is normally classified as negative. The initial discriminant function 90 is optimized so as to achieve the highest possible classification rate, but still many samples are misclassified. Samples located to the left of the initial discriminant function 90 are the samples classified as positive by the discriminant analysis performed up to step P5, and samples located to the right of the initial discriminant function 90 are the samples classified as negative by the discriminant analysis. Accordingly, samples 92 originally negative but classified into the positive class and samples 94 originally positive but classified into the negative class are misclassified samples. The samples 92 will be referred to as the misclassified negative samples and the samples 94 as the misclassified positive samples.

In step P7 of FIG. 6, it is determined whether there is any misclassified sample 92, 94. If there is no misclassified sample 92, 94 at this stage (YES in step P7), it is determined that the two-class classification has been accomplished with a classification rate of 100%, and therefore, the process is terminated at this stage (step P11).

If there is any misclassified sample 92 or 94 in step P7 (NO in step P7), the process proceeds to step P8 to generate and store the AP discriminant function and AN discriminant function. The method for generating the AP discriminant function and AN discriminant function will be described later.

Next, in step P9, the classification of each sample is performed. In step P9, the value of Y of each sample is calculated using each of the two discriminant functions AP and AN generated in step P8, and if the results produced by the two discriminant functions match, it is determined that the sample is correctly classified, and thus the sample is classified into one of the originally intended classes, class 1 (positive class) or class 2 (negative class). If the results produced by the two discriminant functions do not match, the sample is classified into the gray class. This classification has already been described with reference to FIG. 5.

More specifically, the samples classified as positive by both the AP discriminant function 10 and the AN discriminant function 20, i.e., the positive samples located in the region on the left side of the AN discriminant function 20, are determined as the correctly classified positive samples and are therefore classified into class 1, and the negative samples located in the region on the right side of the AP discriminant function 10 are determined as the correctly classified negative samples and are therefore classified into class 2. Any negative or positive sample lying between the two discriminant functions 10 and 20 is classified into the gray class.

In step P10, it is determined whether the number of samples in the gray class is zero or not. If the number of samples in the gray class is zero (YES in step P10), it is determined that all the samples have been correctly classified into the two classes 1 and 2; therefore, the process is terminated at this stage (step P11), and the AP discriminant function and AN discriminant function generated in step P8 are determined as the classification/prediction model.

If NO in step P10, the samples classified into the gray class are extracted (step P12), and a new sample set is formed using the extracted samples. Next, in step P13, STAGE is advanced by 1, and the process starting from step P3 is repeated. The loop from steps P3 to P13 is repeated until the number of misclassified samples becomes zero in step P7 (YES in step P7) or until the number of samples in the gray class becomes zero in step P10 (YES in step P10).

FIG. 10 depicts in the form of an image the process performed in the loop from steps P3 to P13 of FIG. 6. In FIG. 10, AP1, AP2, and AP3 indicates the AP discriminant functions generated in the respective stages, and AN1, AN2, and AN3 indicates the AN discriminant functions generated in the respective stages. In STAGE 1, the samples classified into the gray class are isolated from the population of samples, and in STAGE 2, the samples classified into the gray class in STAGE 1 (the samples located within the region 100) are grouped together to form a new sample set, and the process from steps P3 to P13 is performed to isolate the samples falling in the new gray class (the samples located within the region 102). In STAGE 3 and subsequent stages, the same process is repeated. The process is repeated until the number of samples classified into the gray class becomes zero.

In most cases, the loop from steps P3 to P13 is repeated until the number of samples in the gray class decreases to zero. However, in rare cases, the number of samples in the gray class may not decrease to zero for some reason. To address such cases, the number of stages or the processing time may be limited in advance so that unnecessary processing may be forcefully terminated.

FIG. 11 depicts a table that stores the classification results of the samples in the respective stages and the classes to which the respective samples are finally assigned. Columns 110, 111, 112, 113, and 114 depict information concerning the classes determined for the samples in the respective stages. Column 11 depicts the classes to which the respective samples are finally assigned. The table depicts that, in STAGE 1, for example, when the AP discriminant function AP1 was applied, sample 1 was judged to be negative (−), but when the AN discriminant function AN1 was applied, sample 1 was judged to be positive (+).

Since the two results do not match, sample 1 is classified into the gray class. In STAGE 4, the classification results of sample 1 by the AP discriminant function AP4 and AN discriminant function AN4 both depict negative; therefore, in STAGE 4, sample 1 is classified into the negative class, i.e., class 2. For sample 1, no further classification is performed, and class 2 is determined as the class it belongs to.

For sample 2, the classification results produced by the AP discriminant function AP1 and AN discriminant function AN1 in STAGE 1 both depict negative, so that in STAGE 1, sample 2 is classified into class 2, and no further processing is performed. For sample n, since the classification results produced by the AP and AN discriminant functions coincide in STAGE 5 match, sample n is classified into class 1 in STAGE 5. FIG. 11 depicts the case where the classes of all the samples have been determined by the end of STAGE 5, but if there is any sample whose class has not yet been determined by the end of STAGE 5, STAGE 6 and subsequent stages are performed until the class can be determined.

By repeating the above process, the classes of all the samples are finally determined. A model for predicting the classes of samples whose classes are not known is constructed using the AP discriminant function and AN discriminant function generated in each of the stages needed to determine the classes of the above samples. That is, the AP1/AN1 pair, the AP2/AN2 pair, the AP3/AN3 pair, . . . , the APn/ANn pair are each used as the classification/prediction model for samples of unknown classes. In the case of prediction, if the AP and AN models pregenerated from the respective stages are all used, there may remain a sample or samples whose class are not determined. In this case, the class to which such a sample is finally assigned is the gray class. However, if the last stage has ended with the classification by one discriminant function, not with the classification by the two discriminant functions AP and AN, this means that all the samples have each been assigned to either one of the classes.

FIG. 12 is a table for storing the thus created classification/prediction models. The AP discriminant function and AN discriminant function determined in each stage are stored in pairs. Classification/prediction procedures for samples of unknown classes using such classification/prediction models will be described later.

[Method for Generating the AP Discriminant Function and an Discriminant Function]

The procedures for generating the AP discriminant function and AN discriminant function depicted in step P8 of FIG. 6 will be described below.

Figure 13:
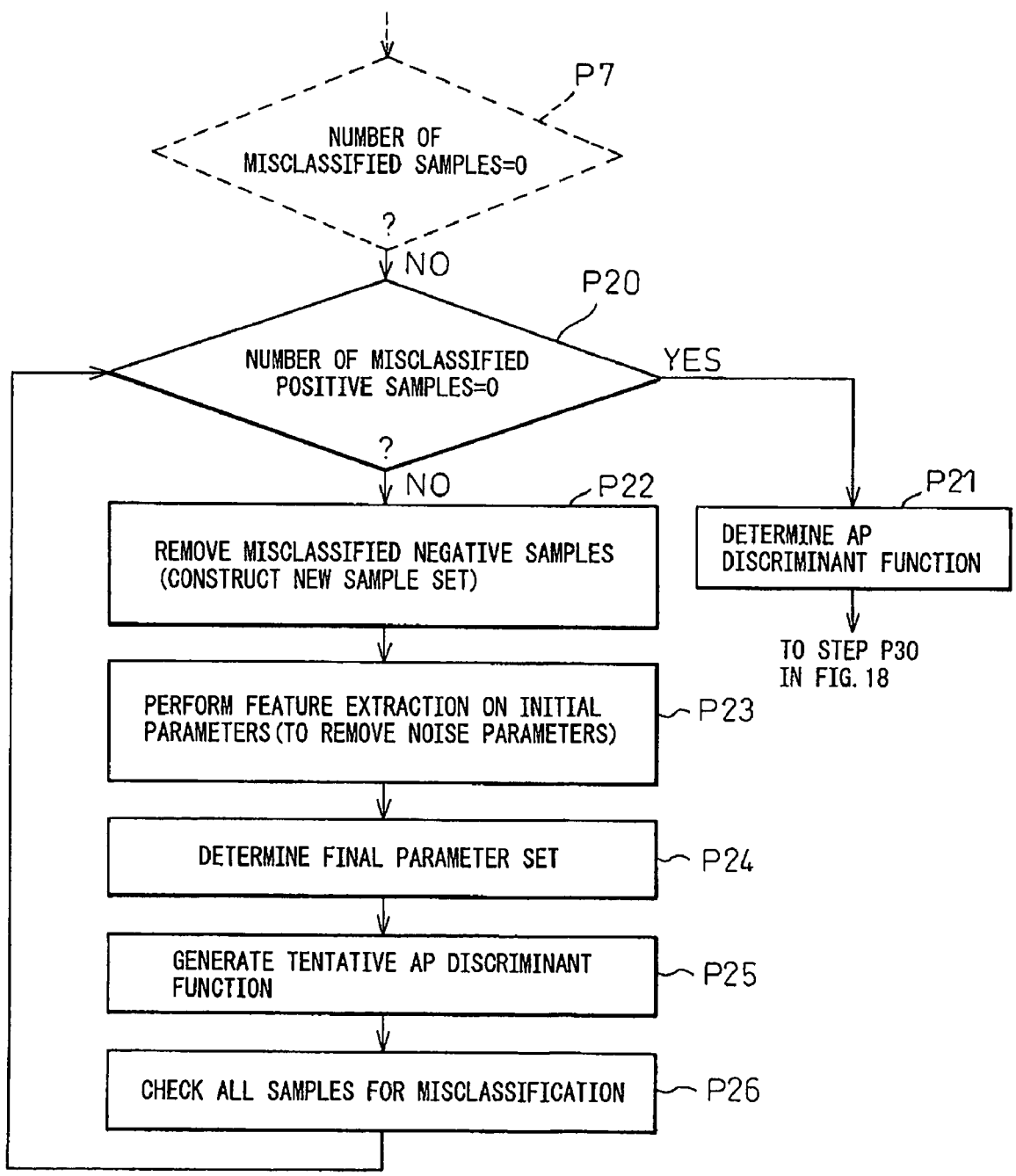
FIG. 13 is a flowchart illustrating a procedure for generating the AP discriminant function.

FIG. 13 is a flowchart illustrating the procedure for generating the AP discriminant function. If it is determined in step P7 of FIG. 6 that there is any misclassified sample (NO in step P7), the generation of the AP discriminant function is started. First, in step P20, a check is made to determine whether there is any misclassified positive sample (94 in FIG. 9). If there is no misclassified positive sample (YES in step P20), the initial discriminant function generated in step P5 is determined as the AP discriminant function for STAGE 1 (step P21), and the process to generate the AN discriminant function for STAGE 1 is started in step P30 depicted in FIG. 18.

Figure 14:
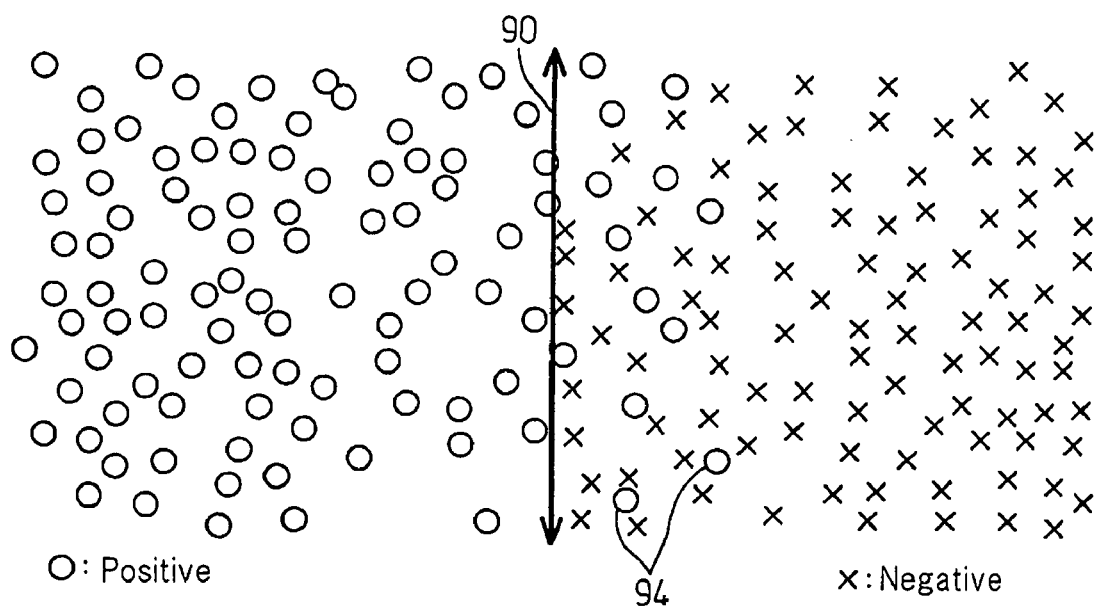
FIG. 14 is an image diagram serving to illustrate the method for generating the AP discriminant function.

If it is determined in step P20 that there is any misclassified positive sample, then processing is performed in step P22 to remove the misclassified negative samples 92 depicted in FIG. 9 from the sample set, thereby forming a new sample set S1. FIG. 14 depicts the relationship between the thus formed new sample set and the initial discriminant function 90. The samples originally positive are all left unremoved, but the negative samples (92 in FIG. 9) misclassified by the initial discriminant function 90 are removed.

In the next step P23, for the new sample set S1 formed in step P22, feature extraction is performed on the initial parameters generated in step P2 of FIG. 6; then, the final parameter set is determined (step P24), and a tentative AP discriminant function is generated by performing discriminant analysis (step P25).

Figure 15:
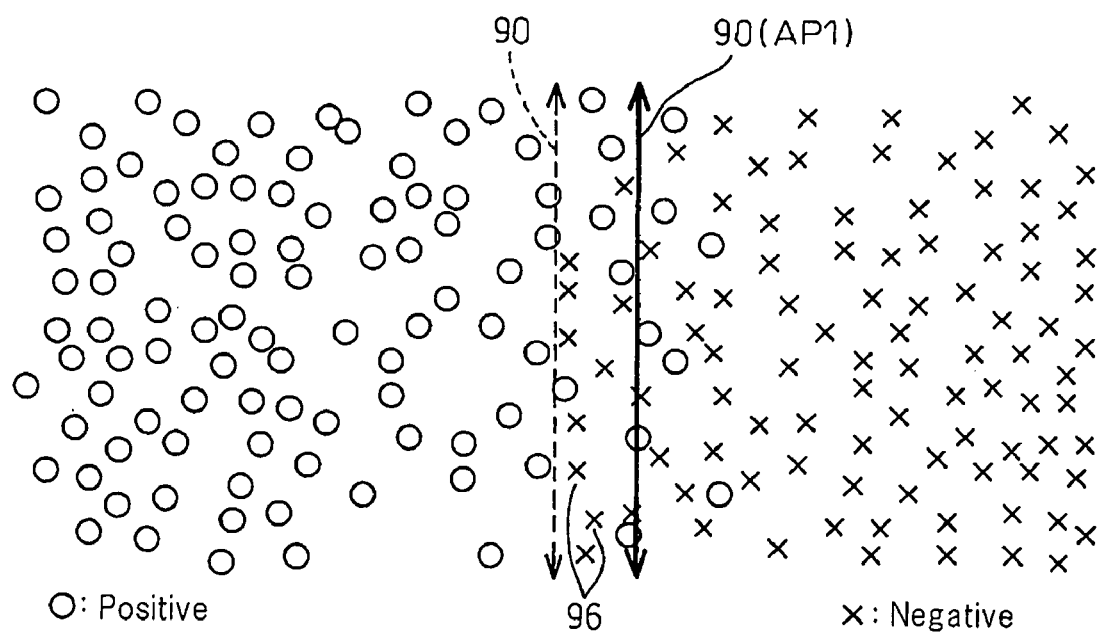
FIG. 15 is an image diagram serving to illustrate the method for generating the AP discriminant function.

FIG. 15 depicts the relationship between the initial discriminant function 90 and the tentative AP discriminant function 90 (AP1) generated in step P25. Since the misclassified negative samples 92 (see FIG. 9) are removed from the sample set S1 in step P22, when a new discriminant analysis is performed in step P25 the generated discriminant function 90 (AP1) moves to the negative side (right side) of the initial discriminant function 90. In step P26, all the samples in the sample set S1 are classified using the newly generated discriminant function, and a check is made to determine whether the samples are correctly classified or not. In the example depicted in FIG. 15, even when the new discriminant function, i.e., the tentative discriminant function 90 (AP1), is applied, there still remain misclassified positive samples 94. Furthermore, as the discriminant function is moved, some of the negative samples correctly classified by the initial discriminant function 90 may turn into misclassified negative samples 96.

Accordingly, after confirming the presence of the misclassified positive samples in step P20 (NO in step P20), the newly developed misclassified negative samples 96 are removed (step P23), thereby forming a new sample set. Thereafter, the loop from step P23 onward is repeated, and eventually, a sample set that does not contain any misclassified positive samples can be obtained.

Figure 16:
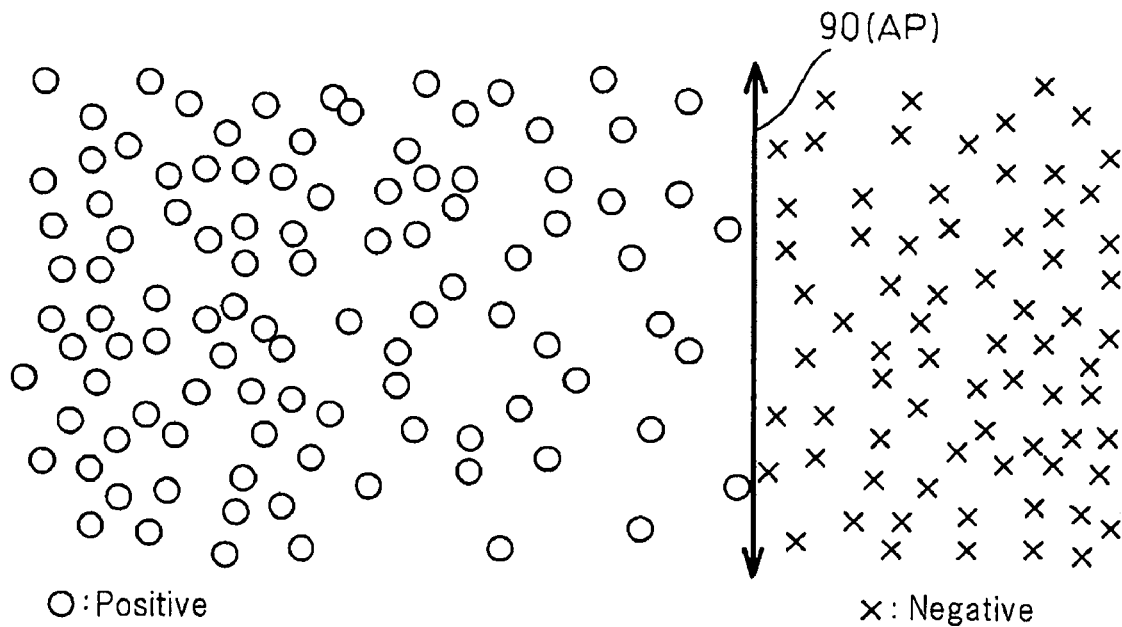
FIG. 16 is an image diagram serving to illustrate the method for generating the AP discriminant function.

FIG. 16 is a diagram depicting the relationship between the thus formed new sample set and the discriminant function 90 (AP) used for the discriminant analysis of that sample set. Since all the positive samples are correctly classified, the discriminant function 90 (AP) is determined as the AP discriminant function for the current stage.

Figure 17:
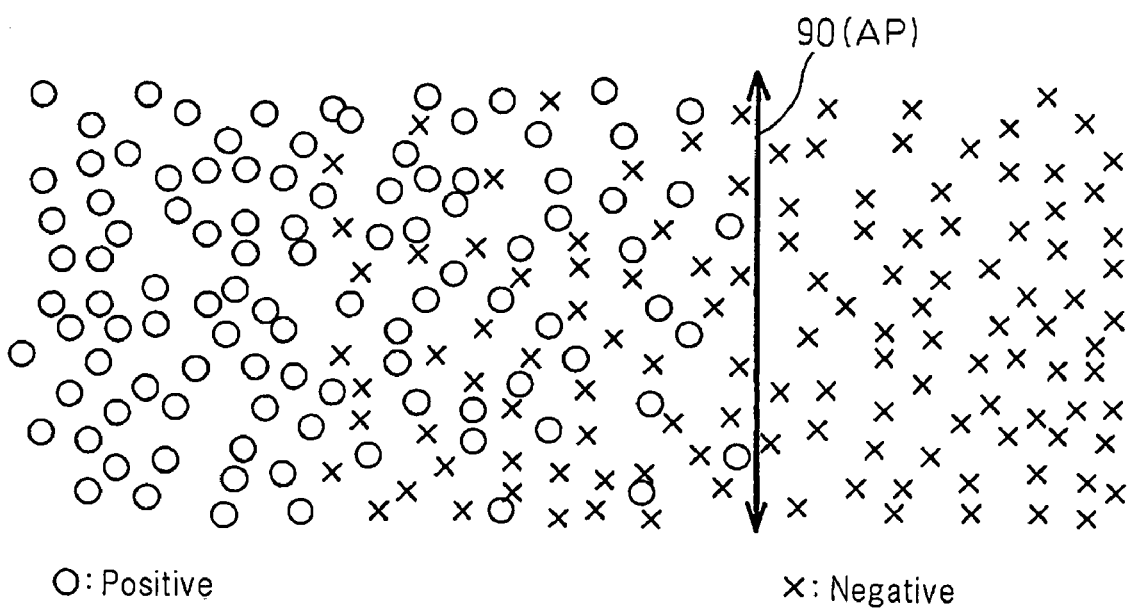
FIG. 17 is an image diagram serving to illustrate the method for generating the AP discriminant function.

FIG. 17 depicts the results of the classification performed on the initial sample set by using the thus obtained AP discriminant function. It can be seen that while all the positive samples are correctly classified by the AP discriminant function 90 (AP), the classification rate of the negative samples is low. The AP discriminant function 90 (AP) here corresponds to the AP discriminant function 10 depicted in FIG. 5.

Figure 18:
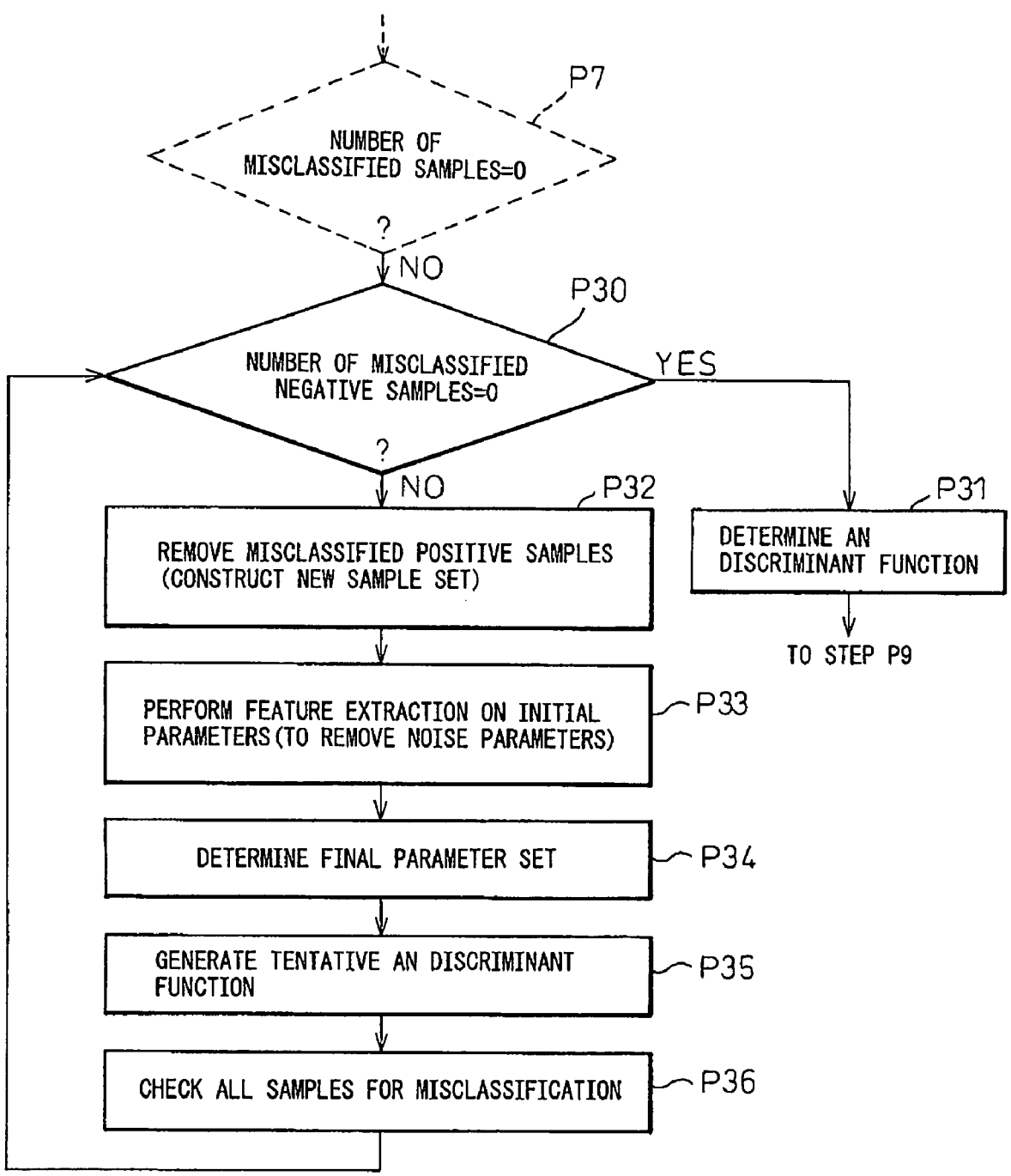
FIG. 18 is a flowchart illustrating a procedure for generating the AN discriminant function.

FIG. 18 depicts a flowchart for generating the AN discriminant function. In step P30, the results of the classification performed using the initial discriminant function are checked to determine whether there is any misclassified negative sample. More specifically, it is determined whether there is any sample (misclassified negative sample) 92 originally negative but mapped to the positive region in FIG. 9, If it is determined in step P30 that there is no misclassified sample (YES in step P30), the initial discriminant function 90 is determined as the AN discriminant function for the current stage (step P31).

If there is any misclassified negative sample in step P30 (NO in step P30), processing is performed to remove the misclassified positive samples 94 in FIG. 9 (step P32). Then, in the same manner as described above for the generation of the AP discriminant function, the AN discriminant function can be obtained by performing step P33 and subsequent steps. In FIG. 18, step P33 corresponds to step P23 in FIG. 13, step P34 corresponds to step P24, step P35 corresponds to step P25, and step P36 corresponds to step P26; since the processing is the same, the description will not be repeated here.

When the AP discriminant function and AN discriminant function are obtained by performing the procedures depicted in FIGS. 13 and 18, the samples are classified into class 1 (positive class), class 2 (negative class), and gray class, respectively, by performing step P9 and subsequent steps depicted in FIG. 6 and, based on the classification results, the classification/prediction models are constructed, as previously described with reference to FIG. 6.

Other features of the above-described two-class classification method will be described below.

[Combinations of Discriminant Functions (Classification Models)]

The generation method of the two discriminant functions (AP discriminant function and AN discriminant function) need not necessarily be the same for all the stages. Furthermore, within the same stage, the generation method of the AP discriminant function and the generation method of the AN discriminant function need not necessarily be the same. The following depicts examples of how the generation methods of the discriminant functions used in the respective stages can be combined in various ways.

1) Within the same stage, the generation method is changed between the AP discriminant function and the AN discriminant function.

Example

STAGE 2

AN discriminant function: Linear learning machine
AP discriminant function: Neural network

STAGE 3

AN discriminant function: Bayes discriminant analysis
AP discriminant function: Discriminant analysis by least squares algorithm 2) Within the same stage, the same generation method is used for the generation of the prediction models, but between the respective stages, different generation methods are used.

Example

STAGE 2

AN discriminant function: Linear learning machine
AP discriminant function: Linear learning machine

STAGE 3

AN discriminant function: Bayes discriminant analysis
AP discriminant function: Bayes discriminant analysis

[System Configuration]

FIG. 19 is a block diagram depicting the system configuration of a two-class classification/prediction model generating apparatus according to one embodiment of the present invention. The two-class classification/prediction model generating apparatus of this embodiment includes an input device 210 for entering sample data and an output device 220 for outputting the classification results or the necessary data being processed. From the input device 200, sample information necessary for classification training is entered into an input data table 310. The input device 200 is also used to enter initial parameter set data into an initial parameter set table 320. If an analyzing unit 400 has an engine 410 for automatically generating the initial parameters for input samples, there is no need to enter the initial parameter set data from the input device 210.

In FIG. 19, reference numeral 330 is a table for storing the final parameter set obtained by performing feature extraction on the initial parameter set. Reference numeral 340 is a table for storing the AP/AN discriminant functions determined for the respective stages.

The analyzing unit 400 includes a controller 420, an initial parameter generating engine 410, a feature extraction engine 430, a discriminant function generating engine 440, a classification result comparator 450, a new sample set generator 460, and an analysis completion condition detector 470. If provisions are made to generate the initial parameters outside the apparatus, the initial parameter generating engine 410 is not needed. The initial parameter generating engine 410 and the feature extraction engine 430 can be implemented using existing ones.

The feature extraction engine 430 determines the final parameter set by performing feature extraction on the initial parameter set, and stores it in the final parameter set table 330. The discriminant function generating engine 440 includes various known discriminant analysis engines and, using the discriminant analysis engine specified by the user or suitably selected by the system, generates the initial discriminant function by performing the discriminant analysis of the input sample while referring to the final parameter set table 330. Further, it generates the AP discriminant function and AN discriminant function based on the initial discriminant function. The classification result comparator 450 compares the classification result produced by the AP or AN discriminant function with the classification result produced by the initial discriminant function, and classifies the samples into class 1, class 2, and gray class. The new sample set generator 460 generates a sample set consisting only of gray class samples, based on the output of the classification result comparator 450.

The feature extraction engine 430, the discriminant function generating engine 440, the classification result comparator 450, and the new sample set generator 460 operate under the control of the controller 420 to carry out the process depicted in FIGS. 6, 13, and 18. The analysis completion condition detector 470 has the function of terminating the classification/prediction model generation process by detecting the instant that the number of samples in the gray class has decreased to substantially zero, or if the number of samples in the gray class does not decrease to zero for any reason, the analysis completion condition detector 470 decides to terminate the process when it is detected that the number of repetitions of the process, i.e., the number of stages, has reached a predetermined number or the processing time has exceeded a predetermined time.

The AP/AN discriminant functions generated for each stage by the analyzing unit 400 are stored in the discriminant function storing table 340 or output via the output device 220. The output format is suitable selected from among USB file, display, printout, etc.

[Classification/Prediction of Samples of Unknown Classes]

FIG. 20 depicts a flowchart of a process for performing the classification/prediction of samples of unknown classes by using the two-class classification/prediction model generated by the method, program, and apparatus of the present invention. In step S50, parameters are set for a sample X of unknown class. In step S51, STAGE is set to 1. In step S52, the classification of the sample X is performed using the discriminant functions stored as the AP and AN discriminant functions for STAGE 1. The classification is performed by calculating the objective variable. In step S53, the classification results produced by the AP and AN discriminant functions are compared, and if the results match (YES in step S53), the sample X is assigned to the matching class (step S54), and the process is terminated (step S55).

If the classification results produced by the AP and AN discriminant functions do not match in step S53 (NO in step S53), STAGE is advanced by 1 in step S56, and after confirming in step S57 that the resulting STAGE is not the final STAGE (NO in step S57), the process returns to step S52 to perform the classification of the sample X by using the AP and AN discriminant functions for the next STAGE.

By repeating the above steps until the classification results match in step S53, the predicted class of the sample X of unknown class is determined. If the classification/prediction of the sample X are not completed even when the STAGE has passed the final STAGEn (YES in step S57), the process is terminated (step S55). The classification/prediction of each sample of unknown class is performed as described above.

INDUSTRIAL APPLICABILITY

The present invention is applicable to any industrial field to which two-class classification can be applied. Main applicable fields are listed below.

1) Chemical data analysis
2) Biotechnology-related research
3) Protein-related research
4) Medical-related research
5) Food-related research
6) Economy-related research
7) Engineering-related research
8) Data analysis aimed at improving production yields, etc.
9) Environment-related research In the field of the chemical data analysis 1), the invention can be applied more particularly to the following researches.

(1) Structure-activity/ADME/toxicity/property relationship research
(2) Structure-spectrum relationship research
(3) Metabonomics-related research
(4) Chemometrics research For example, in the structure-toxicity relationship research field, it is extremely important to predict Ames test results. The reason is that the Ames test is incorporated as one of the most important items into national-level chemical regulations such as industrial safety and health law and chemical examination law defining regulations of toxic chemicals. Any chemical to be marketed is required to pass the Ames test; otherwise, the chemical could not be manufactured in Japan, and the manufacturing activities of chemical companies would halt. Manufacturing overseas and exports of such chemicals are banned by safety regulations in the countries concerned. For example, according to the REACH regulation adopted by the EU Parliament, any company using a chemical is obliged to predict and evaluate the Ames test result of that chemical. The Ames test is a mutagenesis test devised by Dr. Ames, USA, and is a simple method for testing carcinogenicity. It is widely used to measure the safety of many chemicals and products using chemicals.

What is claimed is:

1. A program for generating a two-class classification/prediction model, said program causing a computer to perform a process comprising:
   a) preparing as training data a sample set that contains a plurality of samples belonging to a first class and a plurality of samples belonging to a second class;
   b) generating, by performing discriminant analysis on said sample set, a first discriminant function having a high classification characteristic for said first class and a second discriminant function having a high classification characteristic for said second class;
   c) by classifying said sample set using said first and second discriminant functions, isolating any sample whose classification results by said first and second discriminant functions do not match;
   d) repeating said b) and c) by using a new sample set which is formed by grouping together any sample isolated in said c); and
   e) causing said d) to stop when the number of samples each of whose classification results do not match in said c) has decreased to or below a predetermined value or when the number of repetitions or processing time for repetitions has reached or exceeded a predetermined value.

2. The program according to claim 1, wherein said first discriminant function is generated by carrying out:
   f) generating an initial discriminant function by performing discriminant analysis on said sample set;
   g) generating a new discriminant function by performing discriminant analysis on a new sample set which is formed by removing from said sample set any sample misclassified by said initial discriminant function as being a sample belonging to said first class when said sample is actually a sample belonging to said second class; and
   h) repeating said g) by using said new discriminant function from said g) as said initial discriminant function, until the number of samples misclassified into said first class by said initial discriminant function decreases to substantially zero, and wherein said second discriminant function is generated by carrying out:

i) generating an initial discriminant function by performing discriminant analysis on said sample set;

j) generating a new discriminant function by performing discriminant analysis on a new sample set which is formed by removing from said sample set any sample misclassified by said initial discriminant function as being a sample belonging to said second class when said sample is actually a sample belonging to said first class; and k) repeating said j) by using said new discriminant function from said j) as said initial discriminant function, until the number of samples misclassified into said second class by said initial discriminant function decreases to substantially zero.

3. The program according to claim 1, wherein said e) allows said d) to continue until the number of samples each of whose classification results do not match decreases to substantially zero.

4. The program according to claim 2, wherein said initial discriminant function and said new discriminant function are each generated by performing feature extraction on an initial parameter set pregenerated for said sample set prepared as said training data, thereby forming a final parameter set, and by performing said discriminant analysis using said final parameter set.

5. The program according to claim 1, wherein said first and second discriminant functions determined in said b) after completion of said e) are set up as a classification/prediction model for samples for which it is not known to which class, said first class or said second class, each belongs.

6. A method for generating a two-class classification/prediction model, comprising:
   a) preparing as training data a sample set that contains a plurality of samples belonging to a first class and a plurality of samples belonging to a second class;
   b) generating, by performing discriminant analysis on said sample set, a first discriminant function having a high classification characteristic for said first class and a second discriminant function having a high classification characteristic for said second class;
   c) by classifying said sample set using said first and second discriminant functions, isolating any sample whose classification results by said first and second discriminant functions do not match;
   d) repeating said b) and c) by using a new sample set which is formed by grouping together any sample isolated in said c); and
   e) causing said d) to stop when the number of samples each of whose classification results do not match in said c) has decreased to or below a predetermined value or when the number of repetitions or processing time for repetitions has reached or exceeded a predetermined value, and wherein
      said first and second discriminant functions determined in said b) are set up as a classification/prediction model for samples of unknown classes.

7. The method according to claim 6, wherein said high classification characteristic in said b) provides a classification rate of 95% to 100%.

8. The method according to claim 6, wherein
   said first discriminant function is generated by carrying out:
   f) generating an initial discriminant function by performing discriminant analysis on said sample set;
   g) generating a new discriminant function by performing discriminant analysis on a new sample set which is formed by removing from said sample set any sample misclassified by said initial discriminant function as being a sample belonging to said first class when said sample is actually a sample belonging to said second class; and
   h) repeating said g) by using said new discriminant function from said g) as said initial discriminant function, until the number of samples misclassified into said first class by said initial discriminant function decreases to substantially zero, and wherein
   said second discriminant function is generated by carrying out:
   i) generating an initial discriminant function by performing discriminant analysis on said sample set;
   j) generating a new discriminant function by performing discriminant analysis on a new sample set which is formed by removing from said sample set any sample misclassified by said initial discriminant function as being a sample belonging to said second class when said sample is actually a sample belonging to said first class; and
   k) repeating said j) by using said new discriminant function from said j) as said initial discriminant function, until the number of samples misclassified into said second class by said initial discriminant function decreases to substantially zero.

9. The method according to claim 6, wherein said e) allows said d) to continue until the number of samples each of whose classification results do not match decreases to substantially zero.

10. The method according to claim 8, wherein said initial discriminant function and said new discriminant function are each generated by performing feature extraction on an initial parameter set pregenerated for said sample set prepared as said training data, thereby forming a final parameter set, and by performing said discriminant analysis using said final parameter set.

11. A method for generating a chemical toxicity prediction model, comprising:
   a) preparing as training data a sample set that contains a plurality of chemicals belonging to a first class and a plurality of chemicals belonging to a second class, wherein said chemicals in said first class have a specific kind of toxicity and said chemicals in said second class do not have said toxicity;
   b) generating, by performing discriminant analysis on said sample set, a first discriminant function having a high classification characteristic for said first class and a second discriminant function having a high classification characteristic for said second class;
   c) by classifying said sample set using said first and second discriminant functions, isolating any chemical whose classification results by said first and second discriminant functions do not match;
   d) repeating said b) and c) by using a new sample set which is formed by grouping together any chemical isolated in said c); and
   e) causing said d) to stop when the number of chemicals each of whose classification results do not match in said c) has decreased to or below a predetermined value or when the number of repetitions or processing time for repetitions has reached or exceeded a predetermined value, and wherein
      said first and second discriminant functions determined in said b) after completion of said e) are set up as a classification/prediction model for chemicals of unknown classes.

12. The method according to claim 11, wherein said first discriminant function is generated by carrying out:
f) generating an initial discriminant function by performing discriminant analysis on said sample set;
g) generating a new discriminant function by performing discriminant analysis on a new sample set which is formed by removing from said sample set any chemical misclassified by said initial discriminant function as being a chemical belonging to said first class when said chemical is actually a chemical belonging to said second class; and
h) repeating said g) by using said new discriminant function from said g) as said initial discriminant function, until the number of samples misclassified into said first class by said initial discriminant function decreases to substantially zero, and wherein
said second discriminant function is generated by carrying out:
i) generating an initial discriminant function by performing discriminant analysis on said sample set;
j) generating a new discriminant function by performing discriminant analysis on a new sample set which is formed by removing from said sample set any chemical misclassified by said initial discriminant function as being a chemical belonging to said second class when said chemical is actually a chemical belonging to said first class; and
k) repeating said j) by using said new discriminant function from said j) as said initial discriminant function, until the number of samples misclassified into said second class by said initial discriminant function decreases to substantially zero.

13. The method according to claim 11, wherein said e) allows said d) to continue until the number of samples each of whose classification results do not match decreases to substantially zero.

14. The method according to claim 11, wherein said initial discriminant function and said new discriminant function are each generated by performing feature extraction on an initial parameter set pregenerated for said sample set prepared as said training data, thereby forming a final parameter set, and by performing said discriminant analysis using said final parameter set.

15. An apparatus for generating a two-class classification/prediction model, comprising:
an input device which enters as training data a sample set that contains a plurality of samples belonging to a first class and a plurality of samples belonging to a second class;
a discriminant function generating device which generates, by performing discriminant analysis on said sample set, a first discriminant function having a high classification characteristic for said first class and a second discriminant function having a high classification characteristic for said second class;
a classification result comparing device which classifies said sample set by using said first and second discriminant functions, and isolates any sample whose classification results by said first and second discriminant functions do not match; and
a control device which forms a new sample set by grouping together any sample isolated by said classification result comparing device, and causes said discriminant function generating device and said classification result comparing device to operate repeatedly, and wherein
said control device causes said repeating operation to stop when the number of samples each of whose classification results do not match in said classification result comparing device has decreased to or below a predetermined value or when the number of repetitions or processing time for repetitions has reached or exceeded a predetermined value.

16. The apparatus according to claim 15, wherein said discriminant function generating device generates each of said first and second discriminant functions by performing feature extraction on an initial parameter set pregenerated for said sample set prepared as said training data, thereby forming a final parameter set, and by performing said discriminant analysis using said final parameter set.

17. An apparatus for generating a chemical toxicity prediction model, comprising:
an input device which enters as training data a sample set that contains a plurality of chemicals belonging to a first class and a plurality of chemicals belonging to a second class, wherein said chemicals in said first class have a specific kind of toxicity and said chemicals in said second class do not have said toxicity;
a discriminant function generating device which generates, by performing discriminant analysis on said sample set, a first discriminant function having a high classification characteristic for said first class and a second discriminant function having a high classification characteristic for said second class;
a classification result comparing device which classifies said sample set by using said first and second discriminant functions, and isolates any chemical whose classification results by said first and second discriminant functions do not match; and
a control device which forms a new sample set by grouping together any chemical isolated by said classification result comparing device, and causes said discriminant function generating device and said classification result comparing device to operate repeatedly, and wherein
said control device causes said repeating operation to stop when the number of chemicals each of whose classification results do not match in said classification result comparing device has decreased to or below a predetermined value or when the number of repetitions or processing time for repetitions has reached or exceeded a predetermined value.

18. The apparatus according to claim 17, wherein said control device causes said repeating operation to stop when the number of chemicals each of whose classification results do not match has decreased to substantially zero.

19. The apparatus according to claim 17, wherein said discriminant function generating device generates each of said first and second discriminant functions by performing feature extraction on an initial parameter set pregenerated for said sample set prepared as said training data, thereby forming a final parameter set, and by performing said discriminant analysis using said final parameter set.

20. A classification/prediction method for samples of unknown classes, comprising:
generating a plurality of discriminant function sets each containing a first discriminant function and a second discriminant function, wherein said plurality of discriminant function sets are each generated by carrying out
a) preparing as training data a sample set that contains a plurality of samples belonging to a first class and a plurality of samples belonging to a second class, b) generating, by performing discriminant analysis on said sample set, said first discriminant function which has a high classification characteristic for said first class and said second discriminant function which has a high classification characteristic for said second class;

c) by classifying said sample set using said first and second discriminant functions, isolating any sample whose classification results by said first and second discriminant functions do not match;

d) repeating said b) and c) by using a new sample set which is formed by grouping together any sample isolated in said c); and e) causing said d) to stop when the number of samples each of whose classification results do not match in said c) has decreased to or below a predetermined value or when the number of repetitions or processing time for repetitions has reached or exceeded a predetermined value;

obtaining classification results by applying said first and second discriminant functions contained in a first generated one of said plurality of discriminant function sets to said samples of unknown classes; and sequentially applying said discriminant function sets in order of generation to said samples of unknown classes until said obtained classification results match, wherein the class indicated by said classification results when said classification results match is predicted to be the class to which a corresponding one of said samples of unknown classes belongs.

* * * * *